(12) United States Patent
Gotoh

(10) Patent No.: US 7,339,089 B2
(45) Date of Patent: Mar. 4, 2008

(54) TRANSGENIC ANIMAL EXPRESSING HLA-A24 AND UTILIZATION THEREOF

(75) Inventor: Masashi Gotoh, Osaka-fu (JP)

(73) Assignee: Dainippon Sumitomo Pharma Co., Ltd., Osaka-Shi (JP)

( * ) Notice: Subject to any disclaimer, the term of this patent is extended or adjusted under 35 U.S.C. 154(b) by 0 days.

(21) Appl. No.: 11/319,606

(22) Filed: Dec. 29, 2005

(65) Prior Publication Data

US 2006/0107339 A1    May 18, 2006

Related U.S. Application Data

(62) Division of application No. 10/450,255, filed as application No. PCT/JP01/10885 on Dec. 12, 2001, now abandoned.

(30) Foreign Application Priority Data

Dec. 13, 2000 (JP) ............................. 2000-378556
Sep. 6, 2001  (JP) ............................. 2001-269746

(51) Int. Cl.
   *A01K 67/027* (2006.01)
(52) U.S. Cl. ....................................... 800/18
(58) Field of Classification Search .................. 800/8, 800/18
   See application file for complete search history.

(56) References Cited

OTHER PUBLICATIONS

Alexander et al. (1997) J. Immunol 159 :4753-4761.*
Little et al. (1992) Immunogenetics 35 :41-45.*
Rammensee, Immunogenetics, 1995, vol. 41, p. 178-228).*
Rosenberg, Immunity, vol. 10, pp. 281-287, Mar. 1999.
Kawakami et al., Proc. Natl. Acad. Sci. USA, vol. 91, pp. 3515-1519, Apr. 1994.
Brichard et al., J. Exp. Med., vol. 178, pp. 489-495, Aug. 1993.
Fisk et al., J. Exp. Med., vol. 181, pp. 2109-2117, Jul. 1995.
Shichijo et al., J. Exp. Med., vol. 187, No. 3, pp. 277-288, Feb. 2, 1998.
Price et al., Proc. Natl. Acad. Sci. USA, vol. 88, pp. 1903-1907, Mar. 1991.
Marchand et al., Int. J. Cancer, vol. 80, pp. 219-230, 1999.
Vacchio et al., J. Exp. Med., vol. 185, No. 11, pp. 2033-2038, Jun. 2, 1997.
Baker et al., J. of Exp. Med., vol. 179, pp. 1005-1009, Mar. 1994.
Tsang et al., J. Natl. Cancer Inst., vol. 87, No. 13, pp. 982-990, Jul. 5, 1995.
Barra, C. et al., The Journal of Immunology, vol. 150, No. 9, pp. 3681-3689, May 1, 1993.
Murray, J.D., Theriogenology, vol. 51, pp. 149-159, 1999.
Lariviere, W.R. et al., Journal of Pharmacology and Experimental Therapeautics, vol. 297, No. 2, pp. 467-473, 2001.
Leiter, E.H., Diabetologia, vol. 45, pp. 296-308, 2002.
Houdebine, L.M., Transgenic Research, vol. 9, pp. 305-320, 2000.
Kolb, A.F. et al., Gene, vol. 227, pp. 21-31, 1999.
Bettinotti, M.P. et al., Journal of Immunotherapy, vol. 23, No. 2, pp. 282-287, 2000.
Gotho, M. et al., Int. J. Cancer, vol. 100, pp. 565-570, 2002.
http://www.informatics.jax.org/mgihome/nomen/gene.shtml (2005) pp. 1-21, Mouse Genome Informatics, Rules for Nomenclature of Genes, Genetic Markers, Alleles, and Mutations in Mouse and Rat.
Alexander, J. et al., J. Immunol., vol. 159, pp. 4753-4761, 1997.
Wentworth, P.A., et al., Eur. J. Immunol. vol. 26, pp. 97-101, 1996.
Little, A. et al., Immunogenetics, vol. 35, pp. 41-45, 1992.
Shiku, H. et al., Cancer Chemotheraphy and Pharmacology, vol. 46, pp. S77-S82, 2000.
Correale, P. et al., J. Natil Cancer Inst., vol. 89, pp. 293-300, 1997.
Okugawa, T. et al., Eur. J. Immunol., vol. 30, pp. 3338-3346, 2000.
Itoh, K. et al., Immunology Frontier, vol. 9, pp. 195-203, 1999.
Welker, E. et al., Biochem. Biophys. Res. Commun., vol. 271, pp. 534-536, 2000.

* cited by examiner

*Primary Examiner*—Michael C. Wilson
(74) *Attorney, Agent, or Firm*—Birch, Stewart, Kolasch & Birch, LLP

(57) ABSTRACT

The present invention relates to a non-human transgenic mammal which has had an HLA-A24 gene introduced and in which CTLs are induced when stimulated by an HLA-A24-binding antigen. Such a transgenic mammal provides a method of screening therapeutic or preventive agents for tumors or virus infections by administering a test substance to the transgenic animal and evaluating whether CTLs specific for the test substance are induced. An HLA-A24-binding tumor antigen peptide of PSA origin that is selected by this screening method is described, as are a chimera DNA (DNA construct) useful in the generation of a non-human transgenic mammal, and a host cell transformed by the chimera gene and use thereof.

2 Claims, 23 Drawing Sheets

Fig. 3(A)

|  | 50 | 100 | 150 | 200 | 250 |
|---|---|---|---|---|---|
| HLA-A2402/Kb genome | AAGCTTACTC TCTGGGACCA AACTCCATTG GATGATTTTT CTTCTAGAAG | AGTCCAGGTG GACAGGTAAG GAGTGGGAGT CAGGGAGTCC AGTTCAGGA | CACAGAGATTAC GGGATGAAAA GTGAAAGGAG AGGACGGGG CCCATGCCGA | GGGTTTCTCC CTTGTTTCTC AGACAGCTCT TGGCCAAGA TTCAGGGAGA | CATTGAGACA GAGGGCTTGG CACAGAAGCA GAGGGTCAG GGGAAGTCC |
| HLA-A2402/Kb cDNA | ---------- ---------- ---------- ---------- | ---------- ---------- ---------- ---------- | ---------- ---------- ---------- ---------- | ---------- ---------- ---------- ---------- | ---------- ---------- ---------- ---------- |

Fig. 3(B)

```
HLA-A2402/Kb genome  CAGGGCCCCA GGGGTGGCTC TCAGGGTCTC AGGCCCGAA GGGGGTGTAT   300
HLA-A2402/Kb cDNA    ---------- ---------- ---------- ---------- ----------

HLA-A2402/Kb genome  GGATTGGGGA GTCCCAGCCT TGGGGATTCC CCAACTCGC AGTTTCTTTT    350
HLA-A2402/Kb cDNA    ---------- ---------- ---------- ---------- ----------

HLA-A2402/Kb genome  CTCCCTCTCC CAACCTATGT AGGGTCCTTC TTCCTGATA CTCACGAGCC   400
HLA-A2402/Kb cDNA    ---------- ---------- ---------- ---------- ----------

HLA-A2402/Kb genome  GGACCCAGTT CTCACTCCCA TTGGGTGTCG GGTTCCAGA GAAGCCAATC    450
HLA-A2402/Kb cDNA    ---------- ---------- ---------- ---------- ----------

HLA-A2402/Kb genome  AGTGTGTGTCG CGGTCGCCTGT TCTAAAGTCC GCAGCCACCC ACCGGGACTC  500
HLA-A2402/Kb cDNA    ---------- ---------- ---------- ---------- ----------
```

Fig. 3(C)

```
                                                                              550
HLA-A2402/Kb genome    AGATTCTCCC CAGACGCGA  GCATGGGCGT CATGGGGGCC CGAAGCCTG   28
HLA-A2402/Kb cDNA      ---------- ---------  -ATGGGGT CATGGGGGCC CGAAGCCTG 600
HLA-A2402/Kb genome    TCCTGCTACT CTCGGGGGCC CTGGCCCTGA CCCAGACCTG GGCAG GTGAG   73
HLA-A2402/Kb cDNA      TCCTGCTACT CTCGGGGGCC CTGGCCCTGA CCCAGACCTG GGCAG 650
HLA-A2402/Kb genome    TGCGGGGTCG GGAGGAAAC  GGCCTCTGCG GGAGAAGCA AGGGGCCCC     73
HLA-A2402/Kb cDNA      ---------- ---------  ---------- ---------- ----------

700
HLA-A2402/Kb genome    CTGGCGGGGG CGCAAGACCC GGGAAGCCGC GCCGGGAGGA GGGTCGGGCG   73
HLA-A2402/Kb cDNA      ---------- ---------  ---------- ---------- ----------

750
HLA-A2402/Kb genome    GGTCTCAGCC ACTCCTGTC  CCCAGGCTCC CACTCCATGA GGTATTTCTC   98
HLA-A2402/Kb cDNA      ---------- ---------  -----GCTCC CACTCCATGA GGTATTTCTC
```

Fig. 3(D)

|  | 800 | 850 | 900 | 950 | 1000 |
|---|---|---|---|---|---|
|  | 148 | 198 | 248 | 298 | 343 |

HLA-A2402/Kb genome  CACATGGGTG TTCCTGGGCA GGGGTCCCAG GCCCCGGTTC ATGGGGGTGG
HLA-A2402/Kb cDNA     CACATGGGTG TTCCTGGGCA GGGGTCCCAG GCCCCGGTTC ATGGGGGTGG HLA-A2402/Kb genome  GCTAGTGGA CGACACCAG TTCGTGCGGT TCGACAGGGA CGCGGCGAGC
HLA-A2402/Kb cDNA    GCTAGTGGA CGACACCAG TTCGTGCGGT TCGACAGGA CGCGGCGAGC HLA-A2402/Kb genome  CAGAGGATGG AGCCGCGGGC GCCGTGGATA GAGCAGGAGG GGCCGGAGTA
HLA-A2402/Kb cDNA    CAGAGGATGG AGCCGCGGGC GCCGTGGATA GAGCAGGAGG GGCCGGAGTA HLA-A2402/Kb genome  TTGGGACCAG GAGACACGGA AAGTGAAGGC CCACTCACAG ACTGACCGAG
HLA-A2402/Kb cDNA    TTGGGACCAG GAGACACGGA AAGTGAAGGC GCACTCACAG GCTGACCGAG HLA-A2402/Kb genome  AGAACCTGCG GATCGCGCTC CGTTACTACA ACCAGAGCGA GGCCGGTGAG
HLA-A2402/Kb cDNA    AGAACCTGCG GATCGCGCTC CGTTACTACA ACCAGAGCGA GGCCG-----

Fig. 3(E)

```
HLA-A2402/Kb genome                                                  TGACCCCGGC CCCGGGGGCA GGTCACGACC CCTCATCCCC CACGGACGGG  1050
HLA-A2402/Kb cDNA                                                    ---------- ---------- ---------- ---------- ----------  343

HLA-A2402/Kb genome                                                  CCGGGTCGCC CACAGTCTCC GGGTCCGAGA TCCACCCCGA AGCCGCGGGA  1100
HLA-A2402/Kb cDNA                                                    ---------- ---------- ---------- ---------- ----------  343

HLA-A2402/Kb genome                                                  CCCCGAGACC CTTGCCCCGG GAGAGGCCCA GGGGCCTTAA CCCGGTTTCA  1150
HLA-A2402/Kb cDNA                                                    ---------- ---------- ---------- ---------- ----------  343

HLA-A2402/Kb genome                                                  TTTTCAGTTT AGGCCAAAAA TCCCCCCCGG TTGGTCGGG CCGGGGGGG   1200
HLA-A2402/Kb cDNA                                                    ---------- ---------- ---------- ---------- ----------  343

HLA-A2402/Kb genome                                                  CTCGGGGGAC TGGGCTGACC GCGGGGTCGG GGCCAGTTC TCACACCTC   1250
HLA-A2402/Kb cDNA                                                    ---------- ---------- ---------- GTTC       TCACACCTC   357
```

Fig. 3(F)

| | | | |
|---|---|---|---|
| HLA-A2402/Kb genome<br>HLA-A2402/Kb cDNA | CAGATGATGT TTGGCTTGGA GTGGGGGTCG GACGGGGCCT TCCTTCGGGG<br>CAGATGATGT TTGGCTTGGA CGTGGGGTCG GACGGGGCCT TCCTTCGGGG | 1300<br>407 | |
| HLA-A2402/Kb genome<br>HLA-A2402/Kb cDNA | GTTACGACCAG TACGCCTTACGG ACGGGCAAGA TTTACATGCC CTGAAAGAGG<br>GTTACGACCAG TACGCCTTACGG ACGGGCAAGA TTTACATGCC CTGAAAGAGG | 1350<br>457 | |
| HLA-A2402/Kb genome<br>HLA-A2402/Kb cDNA | ACCTGCGGTC TTGGACCGGG GCGGACATG CGGCTCAGAT CACCAAGGC<br>ACCTGCGGTC TTGGACCGGG GCGGACATG CGGCTCAGAT CACCAAGGC | 1400<br>507 | |
| HLA-A2402/Kb genome<br>HLA-A2402/Kb cDNA | AAGTGGGAGG CGGCCCCATGT GGGGAGCAG CAGAGAGCCT ACCTGGAGGG<br>AAGTGGGAGG CGGCCCCATGT GGGGAGCAG CAGAGAGCCT ACCTGGAGGG | 1450<br>557 | |
| HLA-A2402/Kb genome<br>HLA-A2402/Kb cDNA | CAGGTGCGTG GACGGGCTCC GCAGATACCT GGAGAACGGG AAGGAGACGC<br>CAGGTGCGTG GACGGGCTCC GCAGATACCT GGAGAACGGG AAGGAGACGC | 1500<br>607 | |

Fig. 3(G)

```
HLA-A2402/Kb genome   TCCAGGGCAC GGGTACCAGG GGCCACGGGG CGCCTACCTG ATGCCCTGTA    1550
HLA-A2402/Kb cDNA     TCCAGGGCAG GG---------- ---------- ---------- ----------    619

HLA-A2402/Kb genome   GATCCTGTGT GACACACCTG TACCTTGTCC CCCAGAGTCA GGGGCTGGA      1600
HLA-A2402/Kb cDNA     ---------- ---------- ---------- ---------- ---------      619

HLA-A2402/Kb genome   GTCATTTTCT CTGGCTACAC ACTTAGTGAT GGCTGTGTCAC TTGGACTGAC   1650
HLA-A2402/Kb cDNA     ---------- ---------- ---------- ---------- ----------    619

HLA-A2402/Kb genome   AGTTAATGTT GGTCAGCAAG GTGACTACAA TGGTTGAGTC TCAATGGTGT    1700
HLA-A2402/Kb cDNA     ---------- ---------- ---------- ---------- ----------    619

HLA-A2402/Kb genome   CACCTTCCAG GATCATACAG CCCTAATTTT AATATGAACT CAAACACATA    1750
HLA-A2402/Kb cDNA     ---------- ---------- ---------- ---------- ----------    619
```

Fig. 3(H)

| | | |
|---|---|---|
| HLA-A2402/Kb genome | TTAAATTAGT TATTTTCCAT TCCTCTCTC ATTCTTTGAC TACCTCTCTC | 1800 |
| HLA-A2402/Kb cDNA   | ---------- ---------- ---------- ---------- ---------- | 619 |
| HLA-A2402/Kb genome | ATGCTATTGA ACATCACATA AGGATGCCA TGTTTACCCA ATGGCTCATG | 1850 |
| HLA-A2402/Kb cDNA   | ---------- ---------- ---------- ---------- ---------- | 619 |
| HLA-A2402/Kb genome | TGGATTCCT CTTAGCTTCT GAGTCCCAAA AGAAAATGTG CAGTCCTGTG | 1900 |
| HLA-A2402/Kb cDNA   | ---------- ---------- ---------- ---------- ---------- | 619 |
| HLA-A2402/Kb genome | CTGAGGGGAC CAGCTCTGCT TTTGGTCACT AGTGCGATGA CAGTTGAAGT | 1950 |
| HLA-A2402/Kb cDNA   | ---------- ---------- ---------- ---------- ---------- | 619 |
| HLA-A2402/Kb genome | GTCAAACAGA CACATAGTTC ACTGTCATCA TTGATTAAC TGAGTCTTGG | 2000 |
| HLA-A2402/Kb cDNA   | ---------- ---------- ---------- ---------- ---------- | 619 |

Fig. 3(I)

```
HLA-A2402/Kb genome  GTAGATTCA GTTGTGTCTTG TTAATTGTGT GATTTCTTAA ATCTTCCACA           2050
HLA-A2402/Kb cDNA    ---------  ---------  ---------  ---------  ---------            619

HLA-A2402/Kb genome  CACATTGCCC AAAGGCCCAT GTGACCCATC ACAGCAGACC TGAAGATAAA           2100
HLA-A2402/Kb cDNA    ---ATTGCCC AAAGCCCCAT GTGACCCATC ACAGCAGACC TGAAGATAAA            666

HLA-A2402/Kb genome  GTCACCCTGA GGTGCTGGGC CCTGGGCTTC TACCCTGCTG ACATCAGCCT           2150
HLA-A2402/Kb cDNA    GTCACCCTGA GGTGCTGGGC CCTGGGCTTC TACCCTGCTG ACATCACCCT            716

HLA-A2402/Kb genome  GACCTGGCAG TTGAATGGGG AGGAGCTGAT CCAGGACATG GAGCTTGTGG           2200
HLA-A2402/Kb cDNA    GACCTGGCAG TTGAATGGGG AGGAGCTGAT CCAGGACATG GAGCTTGTGG            766

HLA-A2402/Kb genome  AGACCAGGCC TGCAGGGGAT GGAACCTTCC AGAAGTGGGC ATCTGTGTG            2250
HLA-A2402/Kb cDNA    AGACCAGGCC TGCAGGGGAT GGAACCTTCC AGAAGTGGGC ATCTGTGTG             816
```

Fig. 3(J)

| | | |
|---|---|---|
| HLA-A2402/Kb genome | GTGCCTCTTG GGAAGGAGCA GTATTACACA TGCCATGTGT ACCATCAGGG | 2300 |
| HLA-A2402/Kb cDNA | GTGCCTCTTG GGAAGGAGCA GTATTACACA TGCCATGTGT ACCATCAGGG | 866 |
| HLA-A2402/Kb genome | GCTTGCCTGAG CCCCTCACCC TTGAGATGGG TAAGGAGAGT GTGGGTGCAG | 2350 |
| HLA-A2402/Kb cDNA | GCTTGCCTGAG CCCCTCACCC TTGAGATGGG ---------- ---------- | 895 |
| HLA-A2402/Kb genome | AGCTGGGGTC AGGGAAAGCT GGAGCTTTCT GCAGACCCTG ACTGCTCAG | 2400 |
| HLA-A2402/Kb cDNA | ---------- ---------- ---------- ---------- ---------- | 895 |
| HLA-A2402/Kb genome | GGCTGAGAGC TGGGGTCATG ACCCTCACCT TCATTTCTTG TACCTGTCCT | 2450 |
| HLA-A2402/Kb cDNA | ---------- ---------- ---------- ---------- ---------- | 895 |
| HLA-A2402/Kb genome | TCCCAGCC TCCTCCATCC ACTGTCTCCA ACATGGGGAC CGTTGCTGTT | 2500 |
| HLA-A2402/Kb cDNA | ------AGCC TCCTCCATCC ACTGTCTCCA ACATGGGGAC CGTTGCTGTT | 939 |

Fig. 3(K)

```
HLA-A2402/Kb genome  GTGGTTGTGCC TTTGGAGCTGG AATAGTCACT GGAGCTGTGG TTGGCTTTGT  2550
HLA-A2402/Kb cDNA    GTGGTTGTGCC TTTGGAGCTGG AATAGTCACT GGAGCTGTGG TTGGCTTTGT   989

HLA-A2402/Kb genome  GATGAAGATTG AGAAGGAGAA ACACAGGTAG GAAAGGGCAG AGTCTGAGTT  2600
HLA-A2402/Kb cDNA    GATGAAGATTG AGAAGGAGAA ACACAG----- ---------- ----------  1015

HLA-A2402/Kb genome  TTCTCTCAGC CTCCTTTAGA GTGTGCTCTG CTCATCAATG GGGAACACAG  2650
HLA-A2402/Kb cDNA    ---------- ---------- ---------- ---------- ----------  1015

HLA-A2402/Kb genome  GCACACCCCA CATTGCTACT GTCTCTAACT GGGTCTGCTG TCAGTTCTGG  2700
HLA-A2402/Kb cDNA    ---------- ---------- ---------- ---------- ----------  1015

HLA-A2402/Kb genome  GAACTTCCTA GTGTCAAGAT CTTCCTGGAA CTCTCACAGC TTTTCTCTC   2750
HLA-A2402/Kb cDNA    ---------- ---------- ---------- ---------- ---------   1015
```

Fig. 3(L)

```
HLA-A2402/Kb genome  ACAGTGGAA AAGGAGGGA CTATGCTCTG GCTCCAGTT AGTGTGGGA    2800
HLA-A2402/Kb cDNA    ---GTGGAA AAGGAGGGA CTATGCTCTG GCTCCAGTT ---------    1048

HLA-A2402/Kb genome  CAGAGTTGTC CTGGGACAT TGGAGTGAAG TTGGAGATGA TGGAGCTCT    2850
HLA-A2402/Kb cDNA    --------- --------- --------- --------- ---------    1048

HLA-A2402/Kb genome  GGGAATCCAT AATAGCTCCT CCAGAGAAAT CTTCTAGGTG CCTGAGTTGT    2900
HLA-A2402/Kb cDNA    --------- --------- --------- --------- ---------     1048

HLA-A2402/Kb genome  GCCATGAAAT GAATATGTAC ATGTACACAT GCATATACAT TTGTTTTGTT    2950
HLA-A2402/Kb cDNA    --------- --------- --------- --------- ---------     1048

HLA-A2402/Kb genome  TTACCCTTAG CTCCCAGACC TCTGATCTGT CTCTCCCAGA TTGTAAAGT    3000
HLA-A2402/Kb cDNA    --------G CTCCCAGACC TCTGATCTGT CTCTCCCAGA TTGTAAAG-    1087
```

Fig. 3(M)

| | | | | |
|---|---|---|---|---|
| HLA-A2402/Kb genome | GACACTCTAG GGTCTGATTG GGGAGGGGCA ATGTGGACAT GATTGGGTTT | 3050 |
| HLA-A2402/Kb cDNA | ---------- ---------- ---------- ---------- ---------- | 1087 |
| HLA-A2402/Kb genome | CAGGAACTCC CAGAATCCCC TGTGAGTCAG TGATGGGTTG TTCGAATGTT | 3100 |
| HLA-A2402/Kb cDNA | ---------- ---------- ---------- ---------- ---------- | 1087 |
| HLA-A2402/Kb genome | GTCTTCACAG TGATGGTTCA TGACCTCAT TCTCTAGCTT GAAGACAGCT | 3150 |
| HLA-A2402/Kb cDNA | ---------- TGATGGTTCA TGACCTCAT TCTCTAGCTT GA | 1119 |
| HLA-A2402/Kb genome | GCCTGGAGTG GACTTGGTGA CAGACAATGT CTTCTCATAT CTCCTGTGAC | 3200 |
| HLA-A2402/Kb cDNA | ---------- ---------- ---------- ---------- ---------- | 1119 |
| HLA-A2402/Kb genome | ATCCAGAGCC CTCAGTTCTC TTTAGTCAAG TGTCTGATGT TCCCTGTGAG | 3250 |
| HLA-A2402/Kb cDNA | ---------- ---------- ---------- ---------- ---------- | 1119 |

Fig. 3(N)

```
HLA-A2402/Kb genome    CCTATGGACT CAATGTGAAG AACTGTGGAG CCCAGTCCAC CCCTCTACAC    3300
HLA-A2402/Kb cDNA      ---------- ---------- ---------- ---------- ----------    1119

HLA-A2402/Kb genome    CAGGACCCTG TCCCTGCACT GCTCTGTCTT CCCTTCCACA GCCAACCTTG    3350
HLA-A2402/Kb cDNA      ---------- ---------- ---------- ---------- ----------    1119

HLA-A2402/Kb genome    CTGGTTCAGC CAAACACTGA GGGACATCTG TAGCCTGTCA GCTCCATGCT    3400
HLA-A2402/Kb cDNA      ---------- ---------- ---------- ---------- ----------    1119

HLA-A2402/Kb genome    ACCCTGACCT GCAACTCCTC ACTTCCACAC TGAGAATAAT AATTTGAATG    3450
HLA-A2402/Kb cDNA      ---------- ---------- ---------- ---------- ----------    1119

HLA-A2402/Kb genome    TAACCTTGAT TGTTATCATC TTGACCTAGG GCTGATTTCT TGTTAATTTC    3500
HLA-A2402/Kb cDNA      ---------- ---------- ---------- ---------- ----------    1119
```

Fig. 3(O)

| | | | | |
|---|---|---|---|---|
| HLA-A2402/Kb genome | ATGGATTGAG AATGCTTAGA GGTTTGTCTT GTTGTTGA TTGATTGTT | 3550 |
| HLA-A2402/Kb cDNA   | ---------- ---------- ---------- ---------- ---------- | 1119 |
| HLA-A2402/Kb genome | TTTTTGAAGA AATAAATGAT AGATGAATAA ACTTCCAGAA TCTGGGTCAC | 3600 |
| HLA-A2402/Kb cDNA   | ---------- ---------- ---------- ---------- ---------- | 1119 |
| HLA-A2402/Kb genome | TATGCTGTGT GTATCTGTTG CGACAGGATG AGACTGTAGC AGCTGAGTGT | 3650 |
| HLA-A2402/Kb cDNA   | ---------- ---------- ---------- ---------- ---------- | 1119 |
| HLA-A2402/Kb genome | GAACAGGGCT GTCCCGAGT GGGCTCAGTT TGCTTTGATC TGTGATGGGG | 3700 |
| HLA-A2402/Kb cDNA   | ---------- ---------- ---------- ---------- ---------- | 1119 |
| HLA-A2402/Kb genome | CCACACCTCC ACTGTGTCAC CTCTGGGCTC TGTCCCTCT ATCACTATGA | 3750 |
| HLA-A2402/Kb cDNA   | ---------- ---------- ---------- ---------- ---------- | 1119 |

Fig. 3(P)

```
HLA-A2402/Kb genome   GGCACATGCT GAGAGTTTGT GGTCACAAAG ACACAGGGAA GGCCTGAGCC   3800
HLA-A2402/Kb cDNA     ---------- ---------- ---------- ---------- ----------   1119

HLA-A2402/Kb genome   TTGCCCTGTC CCCAGGATTA GGGCTAAAGA TCAGAGACTC   3850
HLA-A2402/Kb cDNA     ---------- ---------- ---------- ----------   1119

HLA-A2402/Kb genome   GGAATTC   3857
HLA-A2402/Kb cDNA     -------   1119
```

TRANSGENIC ANIMAL EXPRESSING HLA-A24 AND UTILIZATION THEREOF

This application is a Divisional of application Ser. No. 10/450,255 filed on Jun. 12, 2003 now abandoned and for which priority is claimed under 35 U.S.C. § 120. Application Ser. No. 10/450,255 is the national phase of PCT International Application No. PCT/JP01/10885 filed on Dec. 12, 2001 under 35 U.S.C. § 371. The entire contents of each of the above-identified applications are hereby incorporated by reference.

TECHNICAL FIELD

The present invention relates to transgenic animals expressing HLA-A24 and utilization thereof. More specifically, the present invention relates to transgenic animals, into which an HLA-A24 gene has been introduced and in which cytotoxic T lymphocytes are induced when stimulated by an HLA-A24-binding antigen (i.e., HLA-A24-restricted antigen), a method of screening therapeutic or preventive agents for tumors or virus infections using said transgenic animals, HLA-A24-binding tumor antigen peptides of PSA origin selected by said method, recombinant DNA constructs useful in the preparation of transgenic mice and the use thereof, and the like.

BACKGROUND ART

The cellular immunity, particularly cytotoxic T lymphocyte (hereinafter, referred to as "CTL"), plays an important role in the removal of cancer cells or virus-affected cells from living body. CTLs recognize a complex between a peptide fragment of antigen proteins originated from cancer, virus etc. and an MHC class I molecules which is referred to as "HLA" in the case of human, via T-cell receptors, thereby specifically damaging cancer cells or virus-affected cells or activating immune system through the production of various cytokines. A peptide fragment which forms a complex with an MHC class I molecule is referred to as an antigen peptide and is generally about 8-11 amino acids in length. The extracellular domain of an MHC class I molecule consists of $\alpha1$, $\alpha2$ and $\alpha3$ domains, wherein the $\alpha1$ and $\alpha2$ domains participate in the formation of peptide binding groove and the $\alpha3$ domain in the binding with coreceptor CD8 molecule expressed on the surface of CTLS.

Typical examples of tumor antigen protein recognized by CTL comprise those described in Table 1 of *Immunity*, vol. 10: 281, 1999. Specific examples include melanocyte tissue-specific proteins such as gp100 (*J. Exp. Med.*, 179:1005, 1994) and MART-1 (*Proc. Natl. Acad. Sci. USA*, 91:3515, 1994), melanosome antigens such as tyrosinase (*J. Exp. Med.*, 178:489, 1993), and, as tumor antigen proteins other than melanomas, tumor markers such as HER2/neu (*J. Exp. Med.*, 181:2109, 1995), CEA (*J. Natl. Cancer. Inst.*, 87: 982, 1995) and PSA (*J. Natl. Cancer. Inst.*, 89: 293, 1997), and SART-1 (*J. Exp. Med.*, 187: 277, 1998) and cyclophilin B (*Proc. Natl. Acad. Sci. USA*, 88: 1903, 1991) originated from squamous cancer, and the like.

The so-called "cancer vaccine therapy" is considered to be useful in the treatment or prevention of cancer or virus infections, etc., which comprises administering to a subject any of tumor antigen proteins or peptides, or DNAs encoding the same, or virus-originated antigen proteins or peptides so as to enhance specific T cells in vivo. The results of clinical studies conducted with a tumor antigen peptide originated from MAGE-3, which is a tumor antigen protein being overexpressed in melanoma, lung cancer or head and neck cancer, showed significance of vaccine therapy in the tumor rejection (*Int. J. Cancer*, 80: 219,1999).

In the course of development of agents for vaccine therapy, evaluation/determination of a candidate agent for in vivo usefulness in the vaccine therapy cannot be conducted using pure-line mouse commonly used as experimental animals, and requires transgenic animal expressing HLA (hereinafter, it may be referred to as "animal model for human"). That is, human antigen peptide usable in the vaccine therapy should be such peptide that can induce specific immune response when presented to HLA which is a human-specific MHC class I molecule. Accordingly, non-human experimental animals lacking HLA are unavailable for in vivo evaluation of agents for vaccine therapy directed to treatment of human beings. As mentioned above, transgenic animals expressing HLA (animal models for human) are essential for evaluation of usefulness of agents for vaccine therapy.

Although the construction of transgenic animals is technically understood from various basic textbooks, it is not easy to obtain animals (animal models for human) having desired function. There are many cases where intended animal models could not be obtained; for example, a transgene was poorly or never expressed, a transgenic animal lacked desirable functions as an animal model even if a transgene was expressed, etc. Therefore, the construction and/or establishment of animal models for human is considered to be still an unpredictable technique.

As for animal models for HLA, it is considered to be preferred that, when the animal is mouse, the mouse model for human carries a chimera HLA molecule as a transgene, wherein the $\alpha3$ domain of HLA gene is replaced by the corresponding domain of mouse MHC class I molecule, and whereby CTLs of animal models can effectively recognize a complex of HLA and antigen peptide. However, there have been no successful examples regarding animal models for human into which a chimera HLA molecule has been introduced except for two reports, i.e., an animal model for HLA-A2.1 (*Eur. J. Immunol.*, 26: 97, 1996; and "HLA-A2.1/$K^b$ transgenic mouse" in *J. Exp. Med.*, 185: 2034, 1997) and an animal model for HLA-A11 ("HLA-A11/$K^b$ transgenic mouse" in *J. Immunol.*, 159:4753, 1997). These publications showed that the presence or absence of CTL induction in response to the administration of an agent for vaccine therapy in transgenic mice highly correlates with that in human, indicating that the transgenic mice are useful as animal models for human.

The above-mentioned HLA-A2.1 and HLA-A11 are HLA haplotypes dominant in Westerners. As a haplotype that is commonly shared by many Asians including 60% of Japanese, HLA-A24 different from these HLAs is well known. If a mouse model carrying a chimera HLA transgene for HLA-A24 is established, it will become possible to conduct in vivo evaluation of HLA-A24 restricted agent for vaccine therapy widely applicable to Asians, which is expected to greatly contribute to the development of pharmaceutical preparations in this field. However, there have been no reports regarding animal models for HLA-A24, and establishment thereof has been demanded. Such animal models are useful in not only evaluation of vaccine preparations but also screening thereof.

The tumor antigen protein PSA is a glycoprotein that is specifically expressed even in normal prostatic epithelial cells and has a blood half-life of 2-3 day. As the canceration progresses, the expression level of PSA increases to give the tumor antigen protein. Accordingly, PSA is used as a marker in diagnosis of cancer, wherein the PSA level in serum of a patient is measured. The prostatic cancer is placed 1st to 3rd place regarding both the incidence and mortality rate among malignant male tumors in many European countries and the United States, and tends to increase in Japan in the late years. As the prostatic cancer is androgen sensitive, treatment is conducted aiming at removal of androgen (endocrine therapy). However, more than half of the cases of prostatic carcinoma progress to recrudescence carcinoma (i.e., androgen refractory carcinoma) in 5 years, even if it responds to and are controlled by endocrine therapy in the beginning of treatment. Such decrease of androgen dependency greatly hampers endocrine therapy of prostatic cancer. Accordingly, the development of vaccine therapy with an antigen peptide of PSA origin is demanded.

An antigenic peptide region of HLA-A2 type has recently been identified in PSA (*J. Natl. Cancer. Inst.*, 89: 293, 1997). However, there have been no reports showing the existence of an HLA type A24 (HLA-A2402)-binding antigen peptide region. Incidentally, many subtypes belonging to MHC class I molecule exist and it is known that there are certain rules (binding motifs) in the amino acid sequence of antigen peptide having a binding ability. In the binding motif for HLA-A24 above, the second amino acid is tyrosine, phenylalanine, methionine or tryptophan, and the C-terminal amino acid is phenylalanine, leucine, isoleucine, tryptophan or methionine. However, peptides identified on the basis of said motif do not necessarily have the immunogenicity. That is, since an antigen peptide is generated through the intracellular processing of a tumor antigen protein, a peptide not having been produced by in vivo processing cannot be an antigen peptide. Furthermore, even if an amino acid region on a tumor antigen protein identified on the basis of the binding motif is intracellularly generated as a peptide, such a tumor antigen protein may be anergic by reason of, for example, it per se exists in a living organism. As described above, a simple prediction based on the binding motif for a given HLA type is insufficient to identify an antigen peptide, and, from this viewpoint, establishment of a mouse model for human which enables to evaluate an HLA-A24-binding antigen peptides has been demanded.

DISCLOSURE OF INVENTION

One of purposes of the present invention is to provide a novel animal model for HLA-A24 that enables in vivo evaluation of antigenic proteins or peptides and to identify a novel HLA-A24-binding antigen peptide using said animal model, and the like. Specifically, the present invention is aimed at providing a transgenic animal having had an HLA-A24 gene introduced, in which CTLs are induced in response to stimulation with HLA-A24-binding antigen, a method of screening a therapeutic or preventive agent for tumors or virus infections using said transgenic animal, a PSA-originated HLA-A24-binding tumor antigen peptide, etc. selected by the said screening method, and the like.

The present inventors have intensively studied for constructing transgenic animals (animal models for human) so that in vivo evaluation of HLA-A24-binding antigenic proteins or peptides can become possible.

When the present inventors attempted construction of a given transgenic mouse, only one of two literatures above, which is related to HLA-A2.1 (*Eur. J. Immunol.*, 26:97 (1996)), seemed to serve as a useful reference. However, the method described in this literature was inappropriate for achieving the purpose of the present invention. As mentioned above, it has been known a method for generating animal models for HLA by introducing a gene of chimera HLA molecule wherein the α3 domain of HLA is replaced by the same domain of mouse MHC class I molecule (H-2K$^b$, etc.). To obtain an appropriate chimera molecule, restriction sites suited for the ligation with an H-2K$^b$ gene must exist on an HLA molecule. In contrast to HLA-A2.1 gene, HLA-A24 gene does not contain appropriate restriction sites suited for ligating the α1 and α2 domains of said HLA-A24 gene to the α3 domain of mouse MHC(H-2K$^b$) on the genome, and, therefore, an appropriate artificial restriction site had to be constructed. Furthermore, it was totally unpredictable whether or not a genomic DNA of chimera HLA-A24 containing such an artificial sequence is spliced normally to render the expression of the intended chimera HLA-A24 molecule, when introduced into an individual. It was also unclear whether or not the generated transgenic animals can express normally the chimera HLA-A24 molecule and serve as animal models for human having the desired CTL inducing ability. In addition, most of the gene sequence of intron 3 region of mouse H-2K$^b$, which is responsible for the ligation with HLA-A24 gene, was unknown and said gene was hardly available.

Under these circumstances, the present inventors succeeded in the cloning of regions on both the HLA-A24 (HLA-A2402) and mouse H-2K$^b$ genes necessary for the preparation of chimera molecule, ligating these sequences through artificial restriction sites, and constructing a chimera HLA gene (HLA-A2402/K$^b$ gene). The present inventors then attempted to construct an HLA-A2402/K$^b$ transgenic mouse by microinjecting said chimera gene into a fertilized egg of C57BL/6 mouse strain. From 800 or more fertilized eggs undergone microinjection, 8 lines of transgenic mouse were obtained; however, only one line (04-1 line) was revealed to be a transgenic mouse of homo-type that is homozygous for HLA-A24 gene (chimera gene) of the present invention. When the mouse of 04-1 line was stimulated with a known HLA-A24-binding antigen peptide, it showed a satisfactory CTL inducing activity and identified as the objective HLA-A24 transgenic mouse of the present invention.

The present inventors have also succeeded in identifying an HLA-A24-binding tumor antigen peptide of PSA origin that has in vivo antigenicity.

The present invention has been established on the basis of these findings. Thus, the present invention can be summarized as follows:

(1) A non-human transgenic mammal, which has had an HLA-A24 gene introduced and in which CTLs are induced when stimulated by an HLA-A24-binding antigen;

(2) The non-human transgenic mammal according to (1), which comprises the HLA-A24 gene homozygously;

(3) The non-human transgenic mammal according to (1) or (2), wherein the HLA-A24 gene is a chimera gene comprising the α1 and α2 domains of HLA-A24 gene and the α3 domain of mouse MHC class I gene;

(4) The non-human transgenic mammal according to any one of (1)-(3), wherein the HLA-A24 gene is HLA-A2402 gene;

(5) The non-human transgenic mammal according to any one of (1)-(4), wherein the HLA-A24 gene comprises a nucleotide sequence encoding the amino acid sequence shown in SEQ ID NO: 3;

(6) The non-human transgenic mammal according to any one of (1)-(4), wherein the HLA-A24 gene comprises the nucleotide sequence shown in SEQ ID NO: 2;

(7) The non-human transgenic mammal according to any one of (1)-(4), wherein the HLA-A24 gene comprises a nucleotide sequence shown in SEQ ID NO: 1;

(8) The non-human transgenic mammal according to any one of (1)-(4), wherein the HLA-A24 gene is a DNA which hybridizes to the complement of a nucleotide sequence set forth in any one of (5)-(7) above under stringent conditions, and the expression product of said DNA is capable of binding to HLA-A24-binding antigen peptide and inducing CTLs;

(9) The non-human transgenic mammal according to any one of (1)-(8), wherein the non-human mammal is mouse;

(10) The non-human transgenic mammal according to (9) wherein the mouse is of C57BL/6 mouse strain;

(11) A method of screening an agent inducing antigen-specific CTLs, which comprises administering a test substance to a transgenic non-human mammal set forth in any one of (1)-(10) above, and assaying and determining whether CTLs specific for the test substance are induced;

(12) A method of screening a therapeutic or preventive agent for tumors or virus infections, which comprises administering a test substance to a transgenic non-human mammal set forth in any one of (1)-(10) above, and assaying and determining whether CTLs specific for the test substance are induced;

(13) The method of screening according to (11) or (12), which uses a transformant transformed by and expressing the HLA-A24 gene that the transgenic non-human mammal set forth in any one of (1)-(10) contains as a target cell for assaying and determining whether CTLs specific for the test substance are induced;

(14) A transformant transformed by and expressing the HLA-A24 gene which the transgenic non-human mammal set forth in any one of (3)-(10) contains;

(15) A method of screening an antigen-specific CTL inducing agent, which uses the transformant set forth in (14);

(16) A method of screening a therapeutic or preventive agent for tumors or virus infections, which uses the transformant set forth in (14);

(17) An isolated DNA comprising the nucleotide sequence shown in SEQ ID NO: 1;

(18) An isolated DNA comprising the nucleotide sequence shown in SEQ ID NO: 2;

(19) An isolated DNA comprising the nucleotide sequence shown in SEQ ID NO: 3;

(20) An isolated DNA, which hybridizes to the complement of a DNA set forth in any one of (17)-(19) above under stringent conditions and of which expression product is capable of inducing CTLs when bound to an HLA-A24-binding antigen peptide;

(21) The isolated DNA according to (20), which comprises nucleotide sequences each encoding amino acid Nos. 25-114, 115-206 and 207-298 of the amino acid sequence shown in SEQ ID NO: 3;

(22) The isolated DNA according to (20), which comprises polynucleotides each having the sequences corresponding to nucleotide Nos. 72-339, 342-615 and 618-891 of the nucleotide sequence shown in SEQ ID NO: 2;

(23) An expression vector comprising a DNA set forth in any one of (17)-(22) above;

(24) A transformant transformed by the expression vector set forth in (23) above;

(25) A method of screening an antigen-specific CTL inducing agent, which uses the transformant set fort in (24) above;

(26) A method of screening a therapeutic or preventive agent for tumors or virus infections, which uses the transformant set fort in (24) above;

(27) An HLA-A24-binding tumor antigen peptide of PSA origin, which is obtainable by the screening method set fort in any one of (11)-(13) above, or a derivative thereof having functionally equivalent characteristics;

(28) The tumor antigen peptide according to (27), which comprises the amino acid sequence shown in SEQ ID NO: 15, or a derivative thereof having functionally equivalent characteristics;

(29) The tumor antigen peptide according to (28), which comprises the amino acid sequence shown in SEQ ID NO: 17;

(30) A CTL inducing agent comprising as an active ingredient the tumor antigen peptide or a derivative thereof set forth in any one of (27)-(29) above;

(31) A DNA encoding a tumor antigen peptide or a derivative thereof set forth in any one of (27)-(29) above;

(32) A recombinant DNA comprising the DNA set forth in (31) above;

(33) A polypeptide obtainable by expressing the recombinant DNA set forth in (32) above;

(34) A CTL inducing agent comprising as an active ingredient the recombinant DNA set forth in (32) above or a polypeptide set forth in (33) above;

(35) An antigen presenting cell presenting a complex between an HLA-A24 antigen and a tumor antigen peptide or a derivative thereof set forth in any one of (27)-(29) above;

(36) A CTL inducing agent comprising as an active ingredient the antigen presenting cell set forth in (35) above;

(37) A CTL which recognizes a complex between an HLA-A24 antigen and a tumor antigen peptide or a derivative thereof set forth in any one of (27)-(29) above;

(38) A therapeutic or preventive agent for tumors comprising as an active ingredient the tumor antigen peptide or a derivative thereof set forth in any one of (27)-(29) above, the recombinant DNA set forth in (32) above, the polypeptide set forth in (33) above, the antigen presenting cell set forth in (35) above or the CTL set forth in (37) above; and

(39) A diagnosing agent comprising a tumor antigen peptide or a derivative thereof set forth in any one of (27)-(29) above.

BRIEF DESCRIPTION OF DRAWINGS

FIG. 3 (A)-(P) is an alignment of HLA-A2402/K$^b$ genomic sequence described in SEQ ID NO: 1 and HLA-A2402/K$^b$ cDNA sequence described in SEQ ID NO: 2.

The Relationship between sequences in FIG. 3 is shown below.

|  | HLA-A2402/K$^b$ genomic sequence (position) | HLA-A2402/K$^b$ cDNA sequence (position) |
|---|---|---|
| FIG. 3(A) | No. 1-250 |  |
| FIG. 3(B) | No. 251-500 |  |
| FIG. 3(C) | No. 501-750 | No. 1-98 |
| FIG. 3(D) | No. 751-1000 | No. 99-343 |
| FIG. 3(E) | No. 1001-1250 | No. 344-357 |
| FIG. 3(F) | No. 1251-1500 | No. 358-607 |
| FIG. 3(G) | No. 1501-1750 | No. 608-619 |
| FIG. 3(H) | No. 1751-2000 |  |
| FIG. 3(I) | No. 2001-2250 | No. 620-816 |
| FIG. 3(J) | No. 2251-2500 | No. 817-939 |
| FIG. 3(K) | No. 2501-2750 | No. 940-1015 |
| FIG. 3(L) | No. 2751-3000 | No. 1016-1087 |
| FIG. 3(M) | No. 3001-3250 | No. 1088-1119 |
| FIG. 3(N) | No. 3251-3500 |  |
| FIG. 3(O) | No. 3501-3750 |  |
| FIG. 3(P) | No. 3751-3857 |  |

Figure 4:
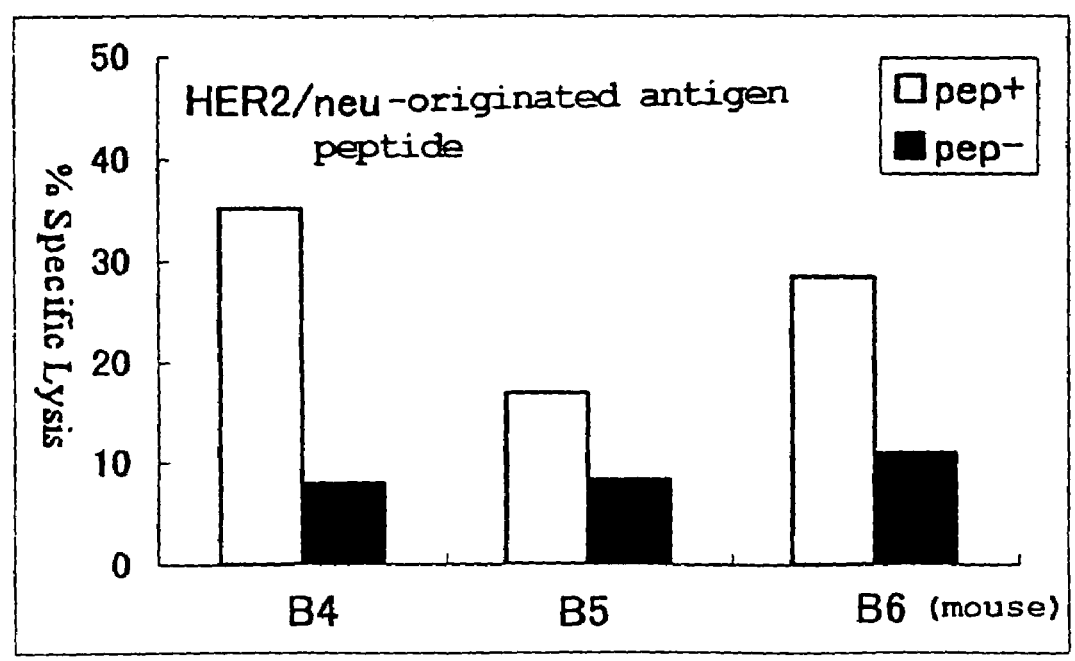

FIG. 4 is a graph showing that specific CTLs were induced when an HLA-A24 expressing transgenic mouse of the present invention was immunized with an HLA-24-binding antigen peptide HER2/neu$_{780-788}$ derived from human tumor antigen HER-2/neu. The cytotoxic activity (% Specific Lysis) and the name of respective transgenic mice are depicted in the vertical and horizontal axes, respectively. In the figure, "pep+" refers to the results obtained using target cells undergone peptide pulse and "pep−" the results obtained using cells without peptide pulse. The sample is a mouse splenocyte preparation prepared by pulsing splenocytes, which have been isolated from an HLA-A24 expressing transgenic mouse immunized with antigen peptide HER2/neu$_{780-788}$, with the same antigen peptide. As the target cells, Jurkat-A2402/K$^b$ cells which are transformants carrying the chimera gene HLA-A2402/K$^b$ and have been labeled with $^{51}$Cr and pulsed with the peptide above (pep$^+$) were used. As control cells, target cells that have not been pulsed with the peptide (pep$^−$) were used.

Figure 5:
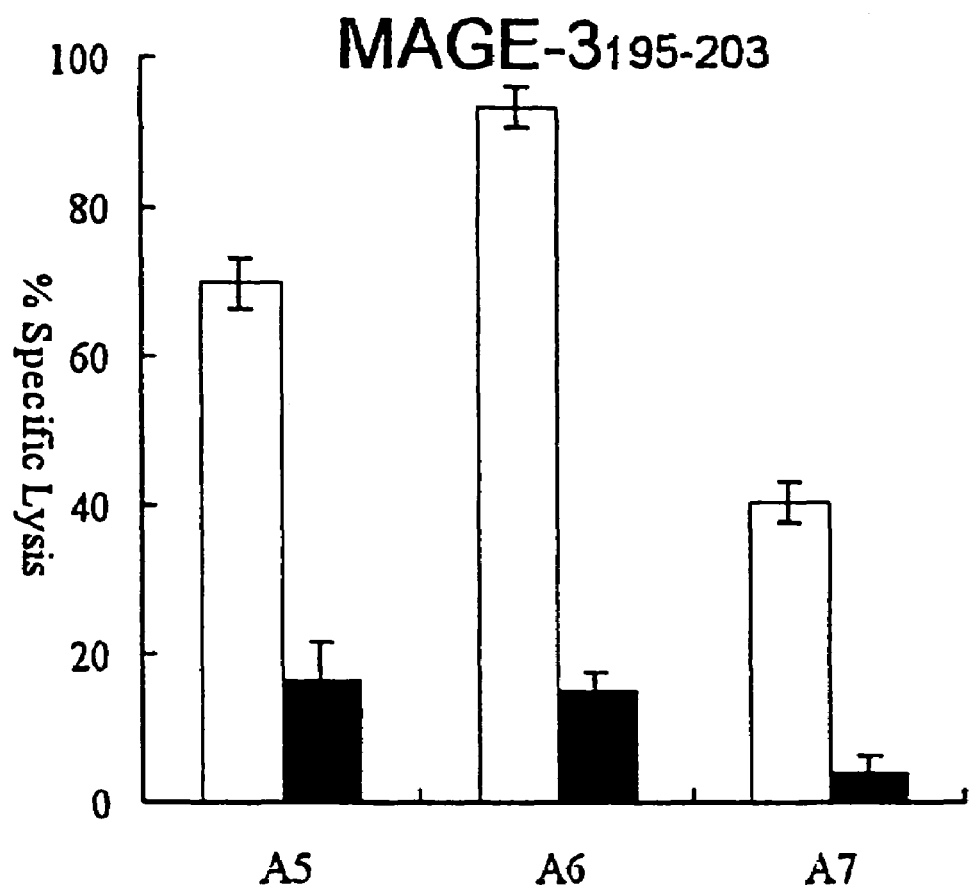

FIG. 5 is a graph showing that specific CTLs were induced when an HLA-A24 expressing transgenic mouse of the present invention was immunized with an HLA-A24-binding antigen peptide MAGE-3$_{195-203}$ derived from cancer antigen MAGE-3. The cytotoxic activity (% Specific Lysis) and the name of respective transgenic mice are depicted in the vertical and horizontal axes, respectively. In the figure, the open bar shows the results obtained using target cells undergone peptide pulse and the solid bar the results obtained using cells without peptide pulse. The sample and the target cells were prepared in a manner similar to that described in regard to FIG. 4 above.

Figure 6:
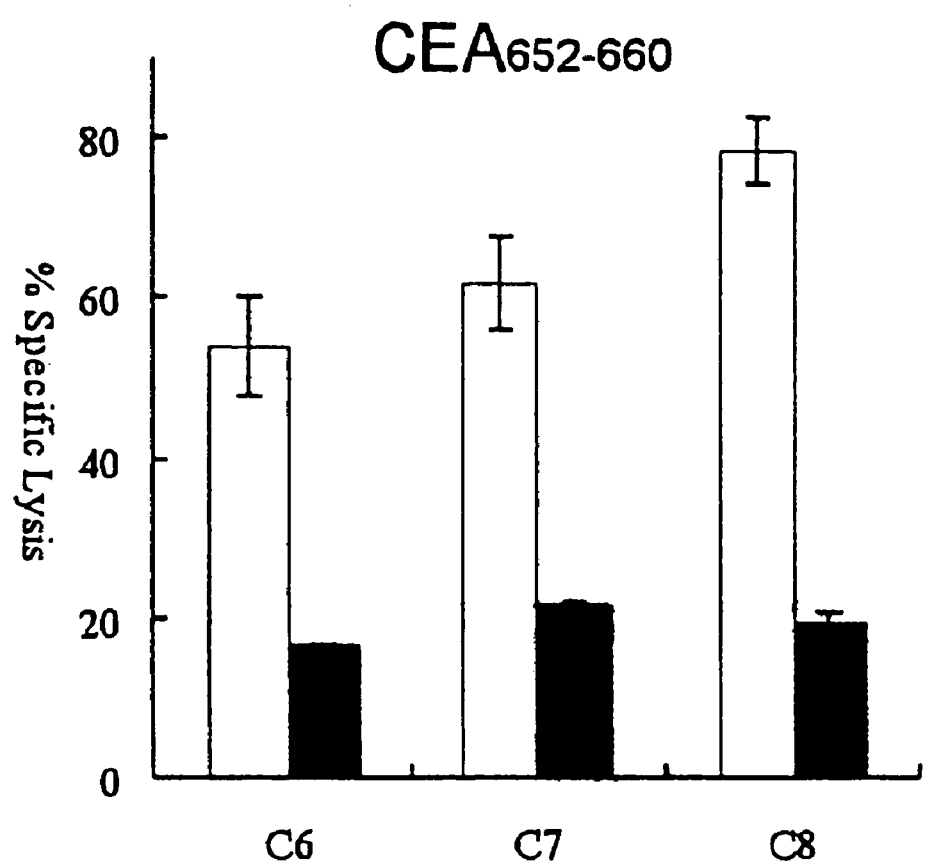

FIG. 6 is a graph showing that specific CTLs were induced when an HLA-A24 expressing transgenic mouse of the present invention was immunized with an HLA-A24-binding antigen peptide CEA$_{652-660}$ derived from cancer antigen CEA. The cytotoxic activity (% Specific Lysis) and the name of respective transgenic mice are depicted in the vertical and horizontal axes, respectively. In the figure, the open bar shows the results obtained using target cells undergone peptide pulse and the solid bar the results obtained using cells without peptide pulse. The sample and the target cells were prepared in a manner similar to that described in regard to FIG. 4 above.

Figure 7:
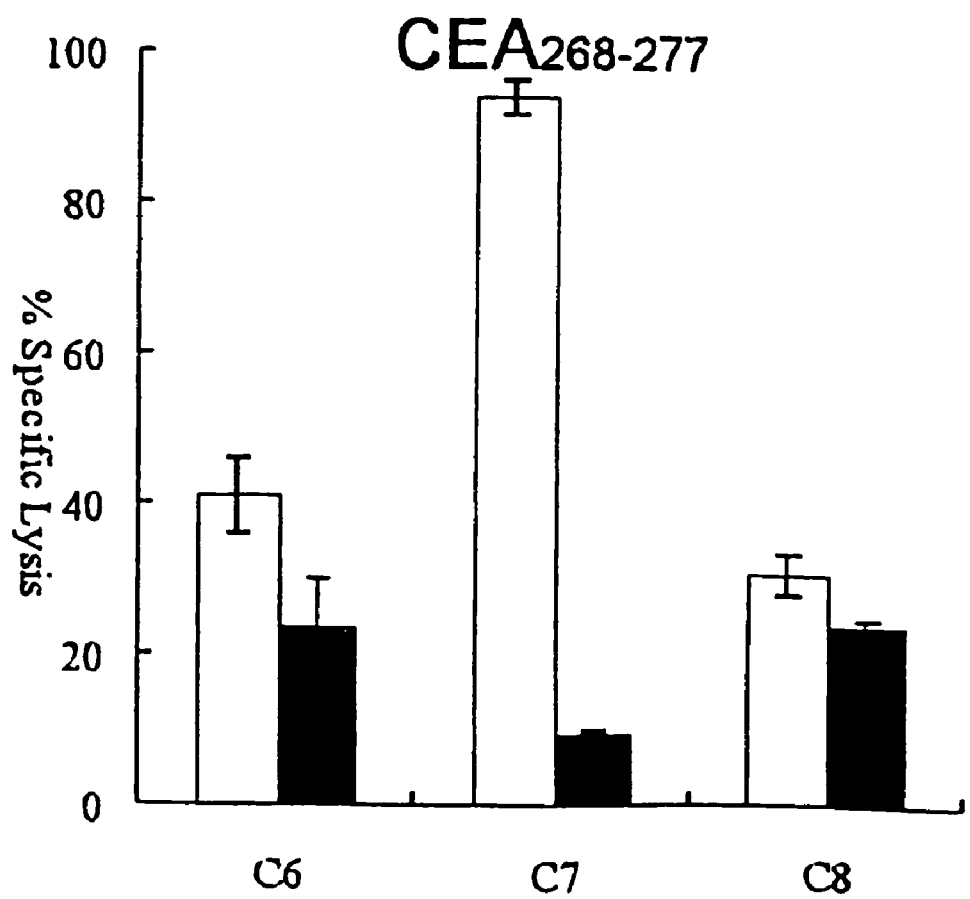

FIG. 7 is a graph showing that specific CTLs were induced when an HLA-A24 expressing transgenic mouse of the present invention was immunized with an HLA-A24-binding antigen peptide CEA$_{268-277}$ derived from cancer antigen CEA. The cytotoxic activity (% Specific Lysis) and the name of respective transgenic mice are depicted in the vertical and horizontal axes, respectively. In the figure, the open bar shows the results obtained using target cells undergone peptide pulse and the and solid bar the results obtained using cells without peptide pulse. The sample and the target cells were prepared in a manner similar to that described in regard to FIG. 4 above.

Figure 8:
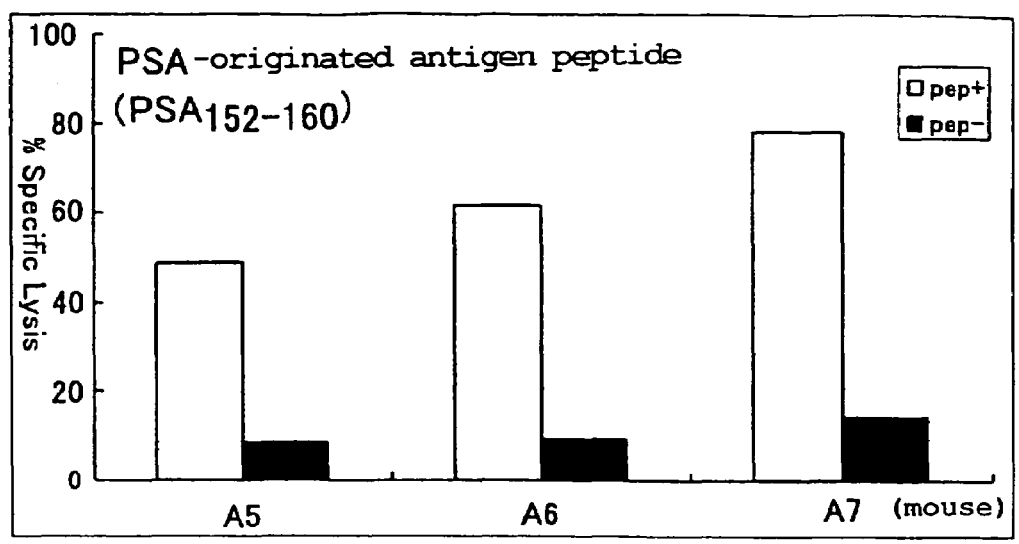

FIG. 8 is a graph showing that specific CTLs were induced when an HLA-A24 expressing transgenic mouse of the present invention was immunized with a PSA-origin antigen peptide PSA$_{152-160}$ prepared from human cancer antigen PSA protein on the basis of information about human HLA-A24-binding motifs. The cytotoxic activity (% Specific Lysis) and the name of respective transgenic mice are depicted in the vertical and horizontal axes, respectively. In the figure, "pep+" refers to the results obtained using target cells undergone peptide pulse and "pep−" the results obtained using cells without peptide pulse. The sample and the target cells were prepared in a manner similar to that described in regard to FIG. 4 above.

Figure 9:
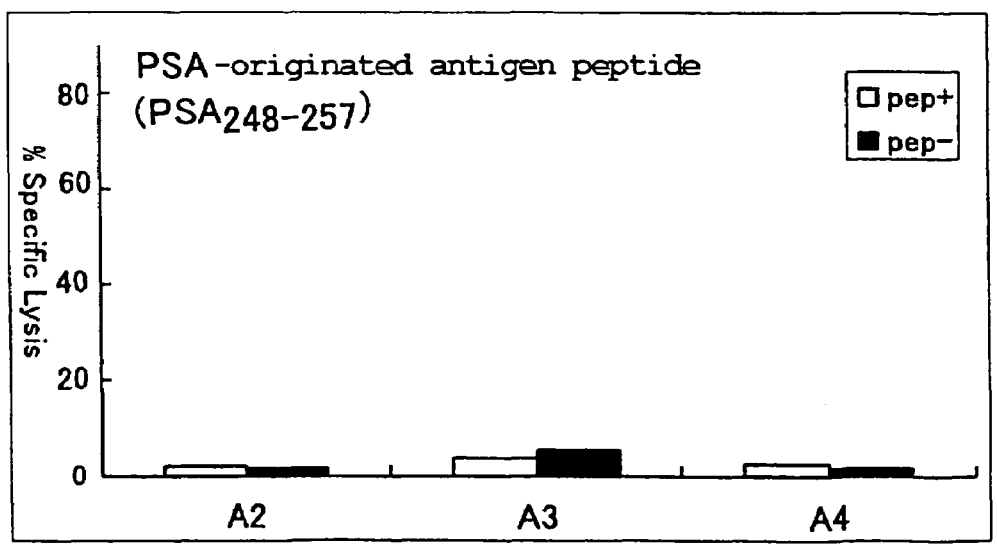

FIG. 9 is a graph showing that specific CTLs were not induced when an HLA-A24 expressing transgenic mouse of the present invention was immunized with a PSA-origin antigen peptide PSA$_{248-257}$ obtained from human cancer antigen PSA protein on the basis of information about human HLA-A24-binding motifs. The cytotoxic activity (% Specific Lysis) and the name of respective transgenic mice are depicted in the vertical and horizontal axes, respectively. In the figure, "pep+" refers to the results obtained using target cells undergone peptide pulse and "pep−" the results obtained using cells without peptide pulse. The sample and the target cells were prepared in a manner similar to that described in regard to FIG. 4 above.

BEST MODE FOR CARRYING OUT THE INVENTION

The present invention for the first time provides a transgenic animal expressing HLA-A24. Specifically, the present invention provides a non-human transgenic animal, into which an HLA-A24 gene has been introduced and in which CTLs are induced when stimulated with an HLA-A24-binding antigen (HLA-A24-restricted antigen peptide).

The present invention also relates to use (utilization) of the above-mentioned transgenic non-human mammal.

The present invention also relates to a DNA construct (e.g., chimera gene) useful in the construction of the above-mentioned non-human transgenic mammal, a host cell transformed by said chimera gene and use thereof.

Examples of an HLA-A24 gene to be introduced when constructing the non-human transgenic mammal of the present invention include subspecies such as HLA-A2402 gene, HLA-A2403 gene, etc. (*J. Immunother.*, 23:282, 2000). However, considering that most of HLA-A24 carriers also contain HLA-A2402 gene, it would be preferred to use HLA-A2402 gene from the aspect of construction of a transgenic animal enabling the in vivo evaluation of an agent for vaccine therapy that is adaptable to many patients. HLA-A2402 and HLA-A2403 genes are registered at GenBank under Accession Nos. M64740 and M64741, respectively. A desired HLA-A24 gene may be cloned by PCR using appropriate primers prepared on the basis of these sequences and, as a template, a genomic DNA or mRNA derived from human tumor cells, etc.

As a transgene, a naturally occurring HLA-A24 gene (genome or cDNA) may be used; however, it is preferred to use a chimera gene wherein the α3 region of said HLA-A24 gene is replaced by the corresponding α3 region of the animal into which it is transferred.

The extracellular domain of an MHC class I molecule consists of α1, α2 and α3 domains, wherein the α1 and α2 domains participate in the formation of peptide binding groove and the α3 domain in the binding with a coreceptor: CD8 molecule expressed on the surface of CTL cells. Besides, it has been suggested to be preferred that an HLA animal model expresses a chimera HLA molecule wherein the α3 domain of HLA gene is replaced by the corresponding domain of MHC of the subject animal so that CTLs of the resultant HLA animal model effectively recognize a complex of HLA and antigen peptide (*Eur. J. Immunol.*, 26: 97, 1996, *J. Immunol.*, 159:4753,1997). Accordingly, as mentioned above, it is preferred that the α3 domain of HLA gene is replaced by the corresponding α3 domain of the subject animal into which it should be introduced.

Such a chimera HLA-A24 gene is also falls within the scope of the "HLA-A24 gene" of the present invention as far as it can be expressed and retain the function as HLA-A24.

For the purposes of the present invention, it is necessary that the α1 and α2 domains of the chimera HLA-A24 gene, which domains participate in the formation of peptide binding groove, are at least derived from HLA-A24. On the other hand, it is preferred that the α3 domain is replaced by the corresponding domain of MHC of the subject animal into which it should be introduced, and it is more preferred that the region including the α3 domain and the succeeding domain thereof is replaced by the corresponding region of MHC of the subject animal into which it should be introduced.

For example, when the subject into which the gene is introduced is a mouse, mouse MHC corresponding to human HLA is H-2 of MHC class I molecule (H-2K$^b$, etc., *Immunogenetics.*, 41:178, 1995). Therefore, preferred examples of HLA-A24 gene to be introduced into a mouse include a chimera HLA-A2402 gene comprising the α1 and α2 domains of HLA-A2402 gene and the α3 domain of mouse H-2K$^b$ gene.

Thus, the term "HLA-A24 gene" herein used in relation to the present invention includes various subspecies belonging to HLA-A24 gene. Examples thereof include not only a naturally occurring HLA-A24 gene comprising all of the α1, α2 and α3 domains composing said HLA-A24 gene but also DNA constructs comprising at least α1 and α2 domains of these three domains. Examples of the DNA construct include a chimera gene consisting of the α1 and α2 domains of HLA-A24 origin and the α3 domain originated from any mammal such as mouse, and the like.

The specific examples of chimera HLA-A2402 gene useful for the present invention include the followings:

(1) A DNA comprising a nucleotide sequence encoding the amino acid sequence shown in SEQ ID NO:3;

(2) A DNA comprising a nucleotide sequence for cDNA shown in SEQ ID NO:2;

(3) A DNA comprising a nucleotide sequence for genomic DNA shown in SEQ ID NO:1;

(4) A DNA which hybridizes to the complement of any one of DNAs set forth in (1)-(3) above under stringent conditions, and of which expression product is capable of binding to HLA-A24-binding antigen peptide and inducing CTLs (i.e., having CTL-inducing activity).

The DNA set forth in (4) refers to a DNA having a similar structure to those set forth in (1) to (3) above (e.g., DNAs comprising modifications of one to several amino acids). Specific examples of such DNA include those hybridizing to the complement of a DNA set forth in any one of (1) to (3) above under stringent conditions and having the above-mentioned activities. In this context, "stringent conditions" refer to, for example, such conditions wherein hybridization is conducted under a condition (formamide concentration: 45% (v/v), salt concentration: 5×SSPE, temperature: 42° C.) and washing is conducted under a condition (salt concentration: 2×SSPE, temperature: 42° C.). The assay for the activity will hereinafter be described. Another example includes a DNA encoding an amino acid sequence, which has substitution, deletion or insertion of one or more amino acid residues (preferably, 1-30 amino acid residues, more preferably 1-20 amino acid residues, still more preferably one to several amino acid residues) in an amino acid sequence encoded by a DNA set forth in (1)-(3) above and which has the above-mentioned activity. Still another example includes a DNA encoding an amino acid sequence which is homologous to an amino acid encoded by a DNA set forth in (1)-(3) above at about 50% or more, preferably at about 70% or more, more preferably at about 80% or more, yet preferably at about 90% or more, and most preferably at about 95% or more homology and which has the above-mentioned activity.

More specifically, examples include a DNA which comprises nucleotide sequences each encoding amino acid Nos. 25-114 (α1 domain), Nos. 115-206 (α2 domain), and Nos., 207-298 (α3 domain) of the amino acid sequence shown in SEQ ID NO: 3 and which has the above-mentioned activity. Further examples include a DNA which comprises nucleotide sequences each corresponding to the nucleotide Nos. 72-339 (α1 domain), Nos. 342-615 (α2 domain), and Nos. 618-891 (α3 domain) of the nucleotide sequence shown in SEQ ID NO: 2.

The process for preparing said chimera HLA-A2402 gene is described below by way of illustration for the preparation of HLA-A24 gene of the present invention, which, however, should not be construed as limiting the scope of the present invention.

A region including promoter, exons 1-3 and introns 1-3, which comprises α1 and a 2 domains needed for the construction of a chimera HLA-A2402 gene is cloned on the basis of sequence information about human HLA-A2402 genomic DNA (GenBank Acc. No. L47206). In this connection, it is desirable that an appropriate restriction site(s) is constructed in the intron 3 so as to facilitate the ligation with mouse H-2K$^b$ gene. Examples of preferred restriction site is BglII site. Said BglII site can be constructed by modifying the downstream primer for PCR reaction so as to generate a BglII site, and conducting PCR reaction using said downstream primer. Specifically, such a modification can be effected using the primer shown in SEQ ID NO: 5.

The aforementioned cloning can be carried out by conducting PCR reaction using, for example, as a template a genomic DNA originated from human tumor cell line and an appropriate primer as mentioned above. Said PCR can be carried out easily according to the teaching in a textbook such as Molecular Cloning 2nd Ed., Cold Spring Harbor Laboratory Press (1989), etc. Also, There are a number of commercially availabe PCR kits at present.

On the other hand, the region downstream from α3 domain (exons 4-8, and introns 3-7) is cloned by PCR using as a template, for example, a genome DNA originated from mouse tumor cell line on the basis of sequence information about mouse H-2K$^b$ genome DNA (GenBank Acc. No. v00746, v00747). The sequence registered at GenBank was incomplete, that is, most of intron 3 region needed for the ligation with HLA-A2402 gene was not registered, and, therefore, the unregistered region had to be cloned and sequenced first of all. Since there exist homologous pseudogenes or highly homologous genes of H-2K$^b$ gene, adequate primers were required to clone appropriate H-2K$^b$ gene. Examples of preferred primer include, for example, various primers described in Example 2 (SEQ ID NO: 6-9).

The thus obtained HLA-A2402 genome fragment and mouse H-2K$^b$ genome fragment are ligated to construct the intended chimera gene (HLA-A2402/K$^b$ gene). When a BglII site is constructed in the intron 3 of HLA-A2402 gene, as mentioned above, the both genes are preferably ligated at said BglII site and the BamHI site in the intron 3 of mouse H-2K$^b$ gene. In this manner, the chimera HLA-A2402 gene (HLA-A2402/K$^b$ gene) of the present invention can be prepared.

The technique for making 1 to several amino acid modifications to the resultant chimera HLA-A2402 gene is also well known to one of ordinary skill in the art and can be conducted according to the method described in a literature such as Molecular Cloning 2nd Edt., Cold Spring Harbor Laboratory Press (1989).

The processes for introducing HLA-A24 gene into fertilized eggs and construction of transgenic animals are hereinafter described.

A region corresponding to HLA-A24 gene is excised from the HLA-A24-containing plasmid constructed above and the resultant fragment is purified in a conventional manner to such a degree that it can be introduced into fertilized eggs. When the HLA-A2402/K$^b$ gene possesses the native promoter region, the excised HLA-A24 gene fragment can be introduced into fertilized eggs as it is; however, when it does not, a foreign promoter necessary for expression should be added. Examples of such a promoter include β-actin promoter, methalothionine promoter, etc. Besides, an enhancer may be added to increase the expression amount and examples of such an enhancer include CMV enhancer, SV40 enhancer, immunoglobulin enhancer, etc.

The purified HLA-A24 gene is then introduced into a fertilized egg of the subject animal. The subject animal may be specifically, for example, mouse, rat, rabbit, etc.; however, rodents such as mouse, rat, etc. are preferred from the viewpoint of feasibility of generation, fosterage and application, and mouse is especially preferred. Above all, a mouse of strain C57BL/6 is more preferred. C57BL/6 mouse strain has an advantage because said mouse expresses H-2K$^b$ as the class I molecule and not H-2K$^d$ having similar binding motif as HLA-A24. That is, when an HLA-A24-binding antigen is administered, there is no danger of presentation of an antigen on the cell surface or cross-reaction.

The construction of transgenic mammal will hereinafter be described using a mouse as an example.

The method for introducing a gene into a mouse fertilized egg includes microinjection, electroporation, etc., without limitation. After introduction, the resultant egg cells are incubated and transferred to oviduct of a foster parent mouse, and the recipient animal is raised. Among the offspring born, those containing the HLA-A24 gene of the present invention are selected to generate the transgenic mouse. The identification of said transgenic mouse can be carried out by, for example, PCR using primers specific for the introduced HLA-A24 gene and a DNA preparation derived from mouse tail as a template.

The so generated transgenic mouse line can be examined whether the introduced HLA-A24 gene is expressed on the cell surface by, for example, recovering splenocytes from spleen isolated from the transgenic mouse and analyzing said splenocytes by flow cytometry. The resultant transgenic mouse of the present invention preferably carries the HLA-A24 transgene homozygously.

The above-mentioned transgenic animals can be generated by making reference to "*Handbook of New Gengenetic Engineering Technique*", p269-276, Yodo-sha (1996), "*Operating Manual for Mouse Embryo*", Kindai-syuppan (1989) and the like. For example, with the aim of integrating a DNA construct, as a chimera HLA-A24 gene, in the HLA-A24 gene locus of mouse genome, said construct is introduced into mouse embryonic stem cells and the resultant recombinant stem cells are then selected and introduced into mouse blastocysts to obtain chimeric embryos. The chimeric embryos are then transferred to pseudo pregnant mice to obtain offspring, which are then screened for the presence of alleles of chimeric transgene to identify the heterozygous mice. The resultant mice are then subjected to crossbreeding to yield homozygous transgenic mice having a phenotype characterized in that CTLs are induced when stimulated with an HLA-A24-binding antigen.

The transgenic mice of the present invention can be examined whether or not they are usable as animal models for human, that is, whether or not specific CTLs are induced in response to stimulation with an HLA-A24-binding antigen by any methods known to one of ordinary skill in the art. Typical example of such methods is provided below.

A known HLA-A24-binding antigen peptide is mixed with Freund's incomplete adjuvant in a conventional manner to prepare water-in-oil emulsion. The emulsion is then used to immunize a transgenic mouse. The inoculation is preferably conducted via mouse tail, subcutaneous of back, peritoneal cavity, plantar, etc. Several days later, the spleen is removed. The splenocytes are then recovered and prepared in a conventional manner. Splenocytes are used herein because they contain antigen-presenting cells such as dendritic cells, but the present invention is not limited to the use of splenocytes.

The splenocytes are then subjected to hemolytic treatment and X-ray irradiation, and then pulsed with the above-mentioned antigen peptide. In so doing, non-irradiated, non-peptide-pulsed splenocytes are also added and re-stimulated at 37° C. Stimulation is continued for several days to obtain a test sample for evaluation.

Target cells for the assay of the test sample above are prepared separately. Any cells expressing HLA-A24 on the cell surface can be used as the target cells, including both of cells naturally expressing HLA-A24 and transformed prepared by introducing HLA-A24 gene.

Examples of cells naturally expressing HLA-A24 include isolated and purified lymphocytes originated from the transgenic mouse of the present invention, RERF-LC-AI cells (Riken Cell Bank, RCB0444) expressing HLA-A24 naturally, etc.

Examples of transformed cells prepared by introducing an HLA-A24 gene include the followings:

The HLA-A24 gene to be transformed into cells may be an HLA-A24 gene of natural-type or a chimera HLA-A24 gene as mentioned above. However, it is preferred to transform a cell by the same HLA-A24 gene as that the transgenic animal contains so as to facilitate the recognition by CTLs of the transgenic animal. That is, when a transgenic animal contains a chimera HLA-A2402 gene (HLA-A2402/K$^b$ gene), it is preferable that an HLA-A2402/K$^b$ gene is transformed into the target cells to be used for the evaluation of said transgenic animal.

The said HLA-A24 gene for transformation may be in the form of cDNA or genomic DNA. In addition, the HLA-A24 may be isolated from the transgenic animal itself or other cells.

For example, when an HLA-A24 cDNA should be introduced, the intended cDNA can be obtained by PCR reaction using HLA-A24 specific primers and mRNA isolated from the transgenic animal as a template. When a genomic DNA should be introduced, the intended genomic DNA can be obtained by PCR reaction using HLA-A24 specific primers and genomic DNA isolated from RERF-LC-AI cells (Riken Cell Bank, RCB0444) expressing HLA-A24 naturally as a template. In addition, the HLA-A24 gene (chimera HLA-A24 gene, etc.) prepared for introducing into transgenic animals above can be used.

Specific examples of cDNA or genomic DNAs to be introduced include DNAs described in (1) to (4) above, that is, a cDNA comprising a nucleotide sequence encoding the amino acid sequence shown in the SEQ ID NO: 3, a cDNA comprising the nucleotide sequence shown in the SEQ ID NO: 2, a genomic DNA comprising the nucleotide sequence shown in the SEQ ID NO: 1, and the like.

The desired recombinant expression vector expressing HLA-A24 can be constructed by inserting the resultant cDNA or genomic DNA into a commercially available expression vector such as pcDNA3.1, pcDNA3.1 derivative, pRc/RSV, pRc/CMV, pEF derivative, pREP9 derivative (Invitrogen), pIRESneo (Chlontech), or the like.

The host cells include human lymphocytes such as Jurkat cell (ATCC T1B-152) and T2 cell (ATCC CRL-1992), and mouse lymphocytes such as EL4 cell (ATCC T1B-39), RMA-S cell (*Nature*., 346:476-80(1990)), K562 cell (ATCC CCL-243), C1R cell (ATCC CRL-2369), and the like. Examples of method for introducing an expression vector containing HLA-A24 gene into host cells include a method utilizing a gene-transfer device, calcium phosphate method (*J. Virol*., 52,456-467(1973)), a method utilizing LT-1 (Pan-Vera Corp.), a method utilizing a lipid for gene transfer (Lipofectamine, Lipofectin; Gibco-BR, Inc.), and the like. When host cells surviving in a selective medium are cultivated, cells expressing a gene introduced stably are established.

The thus established target cells can be used for evaluating/estimating the above-mentioned transgenic animal (i.e., evaluation of test samples derived from the transgenic animal) in a manner well known to a person skilled in the art. Specifically, it can be carried out by a technique wherein the amount of various cytokines (e.g., IFN-γ) produced by CTLs in response to the target cells is measured by ELISA or the like or wherein the cytotoxicity of CTL against target cells is measured ($^{51}$Cr release assay, *Int. J. Cancer*, 58:317, (1994)), which CTLs are induced by stimulation with antigen.

The "$^{51}$Cr release assay" is a technique comprising labeling a target cells with $^{51}$Cr, pulsing the labeled cells with the subject antigen peptide followed by addition of a test sample (splenocytes) of the transgenic animal, and measuring the amount of $^{51}$Cr released from target cells damaged by CTLs. If induction of antigen specific CTLs is recognized by such an assay, the said transgenic animals are estimated to be model animals for human that are capable of evaluating HLA-A24-binding tumor antigen protein or tumor antigen peptide.

The so constructed transgenic animals of the present invention are those wherein CTLs are induced when stimulated by HLA-A24-binding antigen. Accordingly, said transgenic animals are usable for determining whether or not a test substance has an activity of inducing antigen-specific CTLs in vivo. That is, the present invention provides a method of screening a CTL inducing agent specific for an antigen, which comprises administering a test substance to a transgenic animal of the present invention, and assaying and determining whether or not CTLs specific for the test substance are induced.

Examples of the test substance used in the screening method include antigen proteins, which have proved to have activity of inducing specific CTLs by in vitro test, antigen peptides derived therefrom and plasmid DNAs encoding the same, without limitation. Also included are proteins or peptides of which activity is unknown or plasmid DNAs encoding the same.

Specific examples include tumor antigen proteins such as MAGE (*Science*, 254:1643, 1991), gp100 (*J. Exp. Med*., 179: 1005, 1994), MART-1 (*Proc. Natl. Acad. Sci. USA*, 91: 3515, 1994), tyrosinase (*J. Exp. Med*., 178: 489, 1993), HER2/neu (*J. Exp. Med*., 181: 2109, 1995), CEA (*J. Natl. Cancer. Inst*., 87: 982, 1995), PSA (*J. Natl. Cancer. Inst*., 89: 293, 1997), SART-1 (*J. Exp. Med., vol*. 187, p277-288, 1998, WO97/46676), Cyclophilin B (*Proc. Natl. Acad. Sci. U.S.A*., 88:1903, 1991), SART-3 (WO00/12701), ART-1 (WO00/32770), and the like, partial peptides thereof, and plasmid DNAs encoding the same. Additional examples include viruses such as HIV, HCV, HBV, influenza virus, HPV, HTLV, EBV etc., antigen proteins derived from viruses and antigen peptides thereof, antigen proteins derived from bacteria such as tubercle *bacillus* and antigen peptides thereof.

The determination and/or evaluation whether HLA-A24 restricted CTLs specific for a test substance have been induced by administration of said test substance can be carried out in a manner similar to the evaluation method for transgenic animals described above.

For example, the transgenic animal of the present invention is immunized with a test substance, and spleen is extracted and splenocytes are recovered. The splenocytes are subjected to hemolytic treatment and X-ray irradiation, followed by pulsing with a test substance. In so doing, non-irradiated, non-peptide-pulsed splenocytes are also added and re-stimulated at 37° C. Stimulation is continued for several days to yield a test sample for evaluation.

On the other hand, target cells for assay as described above are labeled with $^{51}$Cr, pulsed with antigen peptide of a test substance, and the test sample (splenocytes) above is added thereto. When the induction of antigen specific CTLs in response to the addition of a test sample is observed, said test substance proves to be one having ability to induce antigen specific CTLs in vivo. The CTL inducing agents thus selected can be used as a therapeutic and/or preventive agent for tumors or virus infections.

The target cells described above are used for evaluating not only transgenic animals or test substances administered to transgenic animals, but also any substances which should be evaluated whether they induce HLA-A24 antigen specific CTLs or not.

The present invention also encompasses an HLA-A24-binding tumor antigen peptide of PSA origin, which is obtainable according to the screening method using the transgenic animal of the present invention as described above, and a derivative thereof having characteristics functionally equivalent to that of said tumor antigen peptide. In this regard, the term "PSA" refers to a tumor antigen comprising the amino acid sequence disclosed in *Biochem. Biophys. Res. Commun*. 160(2), 903-910(1989) and GenBank Acc No. M26663.

It has been known that there is a rule (motif) for the sequence of antigen peptides that are presented after binding to HLA antigen, and in the case of HLA-A24 antigen, the amino acid at the second position from the N-terminus of 8 to 11 amino acid peptide is phenylalanine, tyrosine, methionine or tryptophan, and the C-terminal amino acid is phenylalanine, leucine, isoleucine, tryptophan or methionine (*Immunogenetics*, 41: 178, 1995, *J. Immunol.*, 152: p3913, 1994, *J. Immunol.*, 155: 4307,1994). An HLA-A24-binding tumor antigen peptide expressing activity in vivo can be identified and obtained by selecting a partial peptide region on the amino acid sequence of PSA, which region has the binding motif, and applying the selected peptide to the transgenic animal of the present invention.

Specific examples of said tumor antigen peptide include a tumor antigen peptide comprising the amino acid sequence shown in SEQ ID NO: 15.

The tumor antigen peptide of the present invention can be synthesized according to a method generally used in the peptide chemistry. The synthetic method includes those described in literatures (Peptide Synthesis, Interscience, New York, 1966; *The Proteins*, Vol. 2, Academic Press Inc., New York, 1976; *Peptide Gosei (Peptide Synthesis)*, Maruzen, Co. Ltd., 1975; *Peptide Gosei no Kiso to Jikken (Fundamentals and Experiments for Peptide Synthesis)*, Maruzen, Co. Ltd., 1985; Iyakuhin no Kaihatsu (*Developments of Pharmaceuticals*, Sequel Vol. 14, Peptide Gosei (*Peptide Synethesis*), Hirokawa-shoten, 1991), and the like.

In this regard, "a derivative thereof having characteristics functionally equivalent to that of said tumor antigen peptide", which hereinafter may be referred to as "tumor antigen peptide derivative" is a variant that is derived from the tumor antigen peptide of the present invention by modifying one to several amino acid residues in the amino acid sequence of the same and yet has characteristics as a tumor antigen peptide, i.e., being recognized by CTLs when bound to HLA-A24 antigen.

In this regard, the term "modification" of amino acid residue(s) means substitution, deletion and/or addition of amino acid residue(s), including addition of amino acid residue(s) to the N- and/or C-terminus of peptide, and preferably substitution of amino acid residue(s). When the modification is related to amino acid substitution, the number and the position of amino acid residue to be replaced can be selected optionally, as long as an activity as tumor antigen peptide is maintained.

As mentioned above, it has been known that there is a rule (motif) for the sequence of antigen peptide that is presented after binding to HLA antigen, and in the case of HLA-A24 antigen, the amino acid at the second position from the N-terminus of 8 to 11 amino acid peptide is phenylalanine, tyrosine, methionine or tryptophan, and the C-terminal amino acid is phenylalanine, leucine, isoleucine, tryptophan or methionine (*Immunogenetics*, 41:178, 1995 *J. Immunol.*, 152:3913,1994, *J. Immunol.*, 155:4307, 1994). More preferably, in the motif, the second amino acid from the N-terminus is phenylalanine, tyrosine or tryptophan, and the C-terminal amino acid is phenylalanine, leucine, isoleucine or tryptophan. Besides, an amino acid residue(s) having similar properties to amino acids available in the motif may possibly be accepted.

Accordingly, the specific examples of the tumor antigen peptide derivative of the present invention includes a tumor antigen peptide derivative that has been derived by replacing the amino acid at the second and/or C-terminal position of the motif above by an amino acid exchangeable in the motif, and that has an activity as an tumor antigen peptide. The length of the peptide is preferably from about 8 to 11 amino acids considering that it bounds to an HLA-A24 antigen and presented.

Specific examples include a peptide comprising an amino acid sequence wherein the amino acid at the second position of the amino acid sequence shown in SEQ ID NO: 15 is replaced by any one selected from phenylalanine, tyrosine, methionine and tryptophan, and/or the amino acid at the C terminus is replaced by any one selected from phenylalanine, leucine, isoleucine, tryptophan and methionine, as shown in SEQ ID NO: 17, and having an activity as a tumor antigen peptide.

Similar to the tumor antigen peptide of the present invention, the tumor antigen peptide derivative of the present invention can be identified whether or not it has characteristics functionally equivalent to the tumor antigen peptide by synthesizing a candidate peptide according to a method for peptide synthesis, subjecting the resulting peptide to the transgenic animal of the present invention and examining the same for the activity of inducing HLA-A24 restricted CTLs as mentioned above.

The tumor antigen peptide or its derivative of the present invention has, as shown in the Examples below, an activity of inducing CTLs, which CTLs have cytotoxic activity or generate lymphokines and thereby are able to exert antitumor effects. Accordingly, the tumor antigen peptide or its derivative of the present invention can be used as an active ingredient of a therapeutic or preventive agent for tumors. The present invention provides a therapeutic or preventive agent for tumors comprising as an active ingredient a tumor antigen peptide or a derivative thereof. When the therapeutic or preventive agent for tumors of the present invention is administered to a patient who is HLA-A24 positive and PSA-positive, the tumor antigen peptide or a derivative thereof is effectively presented to an HLA-A24 antigen of the antigen-presenting cells, and CTLs specific for the complex of HLA-A24 antigen presented then proliferate and destroy the tumor cells. In this manner, treatment or prevention of tumors would be achieved. Since PSA is expressed in prostate cancer with high frequency, the therapeutic or preventive agent for tumors of the present invention can be used effectively for prostate cancer.

The therapeutic or preventive agent for tumors of the present invention may be administered along with an adjuvant, or may be administered in a particulate dosage form in order to effectively establish the cellular immunity. Examples of available adjuvant include those described in a literature (*Clin. Microbiol. Rev.*, 7:277-289, 1994). In addition, liposomal preparations, particulate preparations in which the peptides are bound to beads having a diameter of several μm, or preparations in which the peptides are attached to lipids, are also usable. Administration may be achieved, for example, intradermally, hypodermically, by intravenous injection, or the like. Although the dose of a tumor antigen peptide or a derivative thereof of the present invention in the preparation may be adjusted as appropriate depending on, for example, the disease to be treated, the age and the body weight of a particular patient, it would be usually from 0.0001 mg to 1000 mg, preferably from 0.001 mg to 1000 mg, more preferably from 0.1 mg to 10 mg of the peptide every several days to every several months.

The present invention also provides a DNA encoding the tumor antigen peptide or a derivative thereof of the present invention. The DNA of the present invention can be synthesized by one ordinary skilled in the art in ease on the basis of the amino acid sequence of the tumor antigen peptide or a derivative thereof of the present invention. Preferred examples of the present DNA include a DNA encoding the amino acid sequence of SEQ ID NO: 15.

The DNA of the present invention can be used effectively in the production of the tumor antigen peptide or a derivative thereof of the present invention. In addition, the DNA of the present invention can also be used effectively for inducing CTLs, i.e., for treating or preventing tumors.

Thus, there has recently been developed a vaccination method which uses a DNA encoding "polytope" wherein plural of CTL-epitopes are ligated as a DNA vaccine. See, for example, *Journal of Immunology*, 160, p1717, 1998 etc. Accordingly, a DNA prepared by ligating one or more DNAs encoding a tumor antigen peptide or a derivative thereof of the present invention and, if desired, a DNA(s) encoding other tumor antigen peptide is inserted into an appropriate expression vector to obtain an active ingredient of a CTL-inducing agent (i.e., therapeutic or preventive agent for tumors). Said DNA resulted from ligation is referred to as "recombinant DNA". In addition to the above-mentioned use of recombinant DNA as a therapeutic or preventive agent, a polypeptide as an expression product of the recombinant DNA in host cells is also useful as an active ingredient of a therapeutic or preventive agent for tumors.

The term "recombinant DNA" can be easily prepared by a method of DNA synthesis or ordinary genetic engineering technique according to the teaching of Molecular Cloning 2nd. Edit., Cold Spring Harbor Laboratory Press (1989), etc. Furthermore, insertion of the recombinant DNA into an expression vector can also be conducted in accordance with the teaching of the aforementioned textbook and the like.

The evaluation whether or not the resultant recombinant DNA of the present invention gives a tumor antigen peptide that can be recognized by CTL after binding to HLA-A24 antigen is also conducted using the transgenic animal of the present invention.

When applying the recombinant DNA of the present invention to the therapeutic or prophylactic agent for tumors, the following methods are usable.

Thus, examples of a method of introducing the recombinant DNA of the present invention into cells include a method which employs viral vectors and those described in literatures (*Nikkei-Science*, April, 1994, p20-45; *Gekkan-Yakuji*, 36(1), 23-48 (1994); *Jikken-Igaku-Zokan*, 12(15), 1994, and references cited therein), and any one of such methods may be applied to the present invention.

Examples of methods which use viral vectors include those wherein the DNA of the present invention is incorporated into DNA or RNA virus such as retrovirus, adenovirus, adeno-associated virus, herpesvirus, vaccinia virus, poxvirus, poliovirus, or Sindbis virus, and then introduced into cells. Among them, the methods using retrovirus, adenovirus, adeno-associated virus, or vaccinia virus are particularly preferred.

Examples of another method include a method wherein expression plasmids are directly injected intramuscularly (DNA vaccination), the liposome method, Lipofectin method, microinjection, the calcium phosphate method, and electroporation. Among them, DNA vaccination and the liposome method are particularly preferred.

In order to make the recombinant DNA of the present invention act as pharmaceutical in practice, one can use either of two methods: in vivo method in which DNA is directly introduced into the body, or ex vivo method in which certain kinds of cells are removed from human, and after introducing DNA into said cells outside of the body, reintroduced into the body (*Nikkei-Science*, April, 1994, p20-45; *Gekkan-Yakuji*, 36(1), 23-48 (1994); *Jikkenn-Igaku-Zokan*, 12(15), 1994; and references cited therein). In vivo method is more preferable.

In the case of in vivo methods, a DNA of the present invention may be administered via any appropriate route depending on the diseases and symptoms to be treated, and other factors. For example, it may be administered via intravenous, intraarterial, subcutaneous, intracutaneous, or intramuscular routes. In the case of in vivo methods, such pharmaceuticals may be administered in various dosage forms such as solution, and they are typically formulated into injections containing a recombinant DNA of the present invention as an active ingredient, which may also include, as needed, conventional carriers. When a recombinant DNA of the present invention is included in liposomes or membrane-fused liposomes (such as Sendai virus (HVJ)-liposomes), such medicines may be in the form of suspension, frozen drug, centrifugally-concentrated frozen drug or the like.

Although the amount of a recombinant DNA of the present invention in such formulations varies depending on, for example, the disease to be treated, the age and body weight of a particular patient, it is usually preferred to administer 0.0001-100 mg, more preferably 0.001-10 mg, of a recombinant DNA of the present invention at every several days to every several months.

When a recombinant DNA of the present invention as described above is administered to a patient, polypeptides corresponding to the said recombinant DNA are expressed to a high extent. Individual tumor antigen peptide resulted from intracellular processing forms a complex with an HLA antigen and presented on the cell surface of antigen presenting cells at high density, and CTLs specific for the complex proliferate efficiently in vivo and destroy tumor cells. The treatment or prevention of tumor would be achieved in this manner. The recombinant DNA of the present invention is especially useful for treatment or prevention of prostate cancer.

In addition, the "polypeptide" as an expression product of the above-mentioned recombinant DNA can be expressed and produced by transforming a host cell with an expression vector constructed by inserting the above-mentioned recombinant DNA into an appropriate expression vector (e.g., pSV-SPORT1 etc.), and culturing the resultant transformant in an appropriate medium. Examples of host cell include prokaryotes such as *Escherichia coli*, unicellular eukaryotes such as yeast, and cells derived from multicellular eukaryotes such as insects or animals. Transformation of host cells with an expression plasmid can be carried out by a known method such as the calcium phosphate method, DEAE-dextran method, or the electric pulse method. The polypeptide thus obtained can be isolated and purified according to standard biochemical procedures. It can be determined whether the said polypeptide gives a tumor antigen peptide(s) capable of being recognized by CTLs when bound to HLA-A24 antigen using the transgenic animal of the present invention.

When using the polypeptide of the present invention as a therapeutic or preventive agent for tumors, the dosage form, administration method and dose are the same as that mentioned above in connection with the tumor antigen peptide or a derivative thereof of the present invention. When the polypeptide of the present invention is administered to a tumor patient, it is uptaken by antigen presenting cells. Individual tumor antigen peptide produced by intracellular processing then forms a complex with an HLA antigen and presented on the cell surface of antigen presenting cells at high density, and CTLs specific for said complex efficiently proliferate in vivo and destroy tumor cells. In this manner, the treatment and prophylaxis of tumors would be achieved. The polypeptide of the present invention is useful especially in the prevention or treatment of prostate cancer.

The present invention also provides an antigen presenting cell on which a complex of an HLA-A24 antigen and a tumor antigen peptide or a derivative thereof of the present invention is presented.

As shown in the working Examples below, a potent cytotoxic activity was observed after stimulation with the peptide of the present invention, which very shows that antigen presenting cells presenting a complex between the peptide of the present invention and an HLA-A24 antigen exist in the lymph node of a transgenic animal, and that CTLs specifically recognize said antigen presenting cells are induced. Such antigen presenting cells on which a complex between an HLA-A24 antigen and the tumor antigen peptide of the present invention is presented can be effectively used in the cell therapy (DC therapy) as described below.

Antigen presenting cells used for cell therapy are prepared as follows. Cells having an antigen-presenting ability are isolated from a tumor patient and pulsed ex vivo with the tumor antigen peptide or its derivative of the present invention, thereby allowing the cells to present a complex between an HLA-A24 antigen and the peptide or its derivative of the present invention. In this regard, the "cell having an antigen-presenting ability" is not restricted to particular one and includes cells on which an HLA-A24 antigen capable of presenting the tumor antigen peptide or a derivative thereof of the present invention is expressed; however, dendritic cells known to have antigen presenting ability are preferred.

In addition, the substance used for pulsing the above-mentioned antigen presenting cells may be in the form of peptide, as mentioned above, and also in the form of recombinant DNA or RNA, or a polypeptide of the present invention.

The antigen presenting cells of the present invention can be prepared by, for example, isolating cells having an antigen-presenting ability from a tumor patient, pulsing ex vivo with the tumor antigen peptide or its derivative of the present invention to form a complex between an HLA-A24 antigen and the peptide above or its derivative (*Cancer Immunol. Immunother.*, 46:82, 1998; *J. Immunol.*, 158: p1796, 1997; *Cancer Res.*, 59: p1184, 1999). In a case where dendritic cells are used, the antigen presenting cells of the present invention can be prepared as follows. Lymphocytes are isolated from peripheral blood of a tumor patient by Ficoll method; adherent cells are separated from non-adherent cells; the adherent cells are then cultured in the presence of GM-CSF and IL-4 to induce dendritic cells; and the dendritic cells are pulsed by culturing with a tumor antigen peptide or a polypeptide of the present invention to yield the antigen presenting cells of the present invention.

When the antigen presenting cells of the present invention is prepared by a process comprising introducing a recombinant DNA of the present invention into the above-mentioned cells having antigen-presenting ability, said process can be carried out in accordance with the teaching in *Cancer Res.*, 56: p5672, 1996 or *J. Immunol.*, 161: p5607, 1998, and the like. Furthermore, RNA, as well as DNA, is usable for the preparation of antigen presenting cells in accordance with the teaching of *J. Exp. Med.*, 184: p465, 1996, and the like.

The present invention also provides a CTL inducing agent (therapeutic agent for tumors) containing as an active ingredient the antigen presenting cell above. Said therapeutic agent preferably contains physiological saline, phosphate buffered saline (PBS), culture medium, or the like in order to stably maintain the antigen presenting cell. Administration may be achieved, for example, intravenously, hypodermically, or intradermally. The dosage can be, for example, the same as that described in the afore-mentioned literatures.

By returning the above therapeutic agent into the patient's body, specific CTLs are efficiently induced in the patient who is positive for both HLA-A24 and PSA, and thereby tumor can be treated. The antigen presenting cells of the present invention are especially useful for treating prostate cancer.

The present invention also provides CTLs that recognize a complex between an HLA-A24 antigen and the tumor antigen peptide or a derivative thereof of the present invention. The CTLs of the present invention may be used effectively in the following adoptive immunotherapy.

In the case of melanoma, it has been observed that an adoptive immunotherapy wherein intratumoral T cell infiltrate taken from the patient himself/herself are cultured ex vivo in large quantities, and then returned into the patient achieves a therapeutic gain (*J. Natl. Cancer. Inst.*, 86:1159, 1994). Furthermore, in mouse melanoma, suppression of metastasis has been observed by stimulating splenocytes in vitro with a tumor antigen peptide TRP-2, thereby proliferating CTLs specific for the tumor antigen peptide, and then administering said CTLs into a mouse carrying grafted melanoma (*J. Exp. Med.*, 185:453, 1997). This resulted from in vitro proliferation of CTLs that specifically recognize the complex between an HLA antigen of antigen presenting cell and the tumor antigen peptide. Accordingly, a method for treating tumors which comprises stimulating in vitro peripheral blood lymphocytes of a patient with a tumor antigen peptide, a derivative thereof, a recombinant DNA or a polypeptide of the present invention to make tumor-specific CTLs proliferate, and returning the CTLs into the patient is believed to be useful.

Furthermore, the present invention also provides a therapeutic agent for tumors containing as an active ingredient the CTLs of the present invention. It is preferred that the therapeutic agent contains physiological saline, phosphate buffered saline (PBS), culture medium, or the like in order to stably maintain CTLs. Administration may be achieved, for example, intravenously, hypodermically, or intradermally. The dosage can be, for example, the same as that described in the afore-mentioned literatures.

By returning the above therapeutic agent into the patient's body, the toxicity of CTLs on tumor cells is enhanced in the patient who is positive for both HLA-A24 and PSA efficiently and destroy the tumor cells, and thereby achieving the treatment of tumor. The CTLs of the present invention are especially useful in the treatment of prostatic cancer.

Besides, the tumor antigen peptide or a derivative thereof, or a polypeptide of the present invention can be used as an ingredient of an agent for diagnosis of tumors. That is, the tumor antigen peptide or its derivative of the present invention can serve as a diagnostic agent which is useful in the detection of an antibody in a sample (such as blood, a tumor tissue, or the like) obtained from a patient suspected to have a tumor. In this manner, one can detect tumors in early-stage, or diagnose recurrent or metastatic tumors. Furthermore, it may be used for screening of tumor patients adaptable to pharmaceuticals containing tumor antigen peptides or the like of the present invention as an active ingredient. Specifically, the diagnosis can be effected using immunoblotting, RIA, ELISA, or fluorescent or luminescent assay. The diagnostic agent of the present invention is especially useful in the diagnosis of prostatic cancer.

Furthermore, there have recently been established a new method of detecting antigen-specific CTLs that uses a complex between an antigen peptide and an HLA antigen (*Science*, 274: p94, 1996). A complex of a tumor antigen peptide or its derivative of the present invention and an HLA antigen may be applied to the said detection method to detect CTLs specific for tumor antigen whereby one can detect tumors in early-phase, or diagnose recurrence or metastasis of tumor. It can also be used for selecting patients adaptable to the pharmaceuticals of the present invention or for evaluating therapeutic effects thereof, which pharmaceuticals contain as an active ingredient a tumor antigen peptide or the like of the present invention. Thus, the present invention provides a diagnostic agent for tumors comprising a tumor antigen peptide or its derivative of the present invention.

Specifically, the diagnosis above can be carried out as follows: a tetramer of a complex between tumor antigen peptide and fluorescence-labeled HLA antigen obtained by a method described in *Science*, 274: p94, 1996 is prepared and subjected to the flowcytometry and the amount of CTLs specific for antigen peptide among peripheral blood lymphocytes derived from a patient suspected to have a tumor is determined.

The following Examples are provided to further illustrate the present invention and are not to be construed as limiting the scope thereof.

EXAMPLE 1

Cloning of HLA-A2402 Genomic DNA Fragment (1) Cloning of HLA-A2402 Genomic DNA Fragment For the purpose of cloning human HLA-A2404 genomic DNA by PCR, a human tumor cell line, RERF-LC-AI cells (Riken Cell Bank RCB0444) were cultured and human genomic DNA was purified using Genomic Prep Cells and Tissue DNA Isolation Kit (Amersham) as per attached protocol. GenBank database was then searched for HLA-A2402 genomic DNA needed for the construction of chimeric HLA gene, which revealed that one registered under Accession No. Z72422 was relevant, but a 270 bp promoter region was not registered. The construction of the objective transgenic mouse requires promoter, exons 1-3 and introns 1-3. To clone HLA-A2402 genomic DNA containing promoter, PCR was conducted using the upstream primer HLA26-1F:

```
                               (36mer, SEQ ID NO:4)
5'-CCC AAG CTT ACT CTC TGG CAC CAA ACT CCA TGG

GAT-3'
``` which was designed making reference to the nucleotide sequence of the promoter of HLA-A2601 (Accession No. AB005048) frequently found in Japanese; and the downstream primer A24-BglII 30:

```
                               (30mer, SEQ ID NO:5)
   5'-CGG GAG ATC TAC AGG CGA TCA GGT AGG CGC-3'
``` which comprises a modification in the nucleotide sequence in intron 3, specifically, the nucleotide at 1282 position from the 5' terminus of Accession No. Z72422 is changed from G to A. Said modification of nucleotide was needed for the following reasons. The present invention is aimed at obtaining an transgenic mouse expressing a chimeric HLA consisting of exons 1-3 of HLA-A2402 and exons 4-8 of H-2K$^b$, which chimeric HLA can be constructed by ligating the region upstream from the BamHI restriction site in intron 3 of HLA-A2402 genomic DNA and the region downstream from intron 3 of H-2K$^b$ genomic DNA and, for this end, it was necessary to construct an artificial BglII restriction site in the intron 3 of HLA-A2402.

PCR cloning of HLA-A2402 genomic DNA fragment was then conducted using Native Pfu DNA Polymerase (Stratagene) having high 3'→5' exonuclease activity as per attached protocol, and the pair of primers above. The PCR comprised heat treatment at 95° C. for 45 seconds, 35 cycles of reaction at 95° C. for 45 seconds, 66° C. for 1 minute and 72° C. for 4 minutes, and reaction at 72° C. for 10 minutes, followed by cooling to 4° C. The amplified gene fragment was ligated into HindIII and BamHI restriction sites of phagemid vector pBluescript to obtain a recombinant plasmid. The recombinant plasmid was introduced into *E. coli* JM109 (Toyobo) by heat shock method at 42° C., and white colonies of *E. coli* to which the recombinant plasmid has been introduced were selected on ampicillin (50 μg/ml)-containing LB agar medium (1% bacto-tryptone, 0.5% yeast extract, 1% NaCl, 2% agar) coated with X-Gal and IPTG to obtain the transformants.

(2) Determination of Nucleotide Sequence of HLA-A2402 Promoter Region

Four transformants obtained in the above were incubated overnight in LB medium containing ampicillin (3 ml), followed by purification of plasmid clone contained in each transformant by alkaline lysis method (CURRENT PROTOCOLS IN MOLECULAR BIOLOGY, edited by F. M. Ausubel, et al., John Wiley & Sons, Inc.). The nucleotide sequence was then determined by means of ABI PRISM™ 377 DNA Sequencing System (PE Biosystems). Samples for sequencing were subjected to ABI PRISM™ Dye Terminator Cycle Sequencing Ready Reaction kit (PE Biosystems) to sequence each clone as per attached protocol. When the promoters of respective clones were compared, it was revealed that they are totally the same. Thus, the nucleotide sequence of promoter region of HLA-A2402 was determined, which sequence had not been registered at GenBank database. The nucleotide sequence registered under the Accession No. Z72422 was compared with that of respective clones, which revealed that there is one normal clone free of PCR mutation.

EXAMPLE 2

Cloning of H-2K$^b$ Genomic DNA Fragment (1) Cloning of H-2K$^b$ Genomic DNA Fragment Mouse tumor cell line EL4 (ATCC T1B-39) was cultured, and mouse genomic DNA was purified and used in the PCR cloning. Purification of DNA was carried out using TaKaRa LA Taq™ (Takara Shuzo) suited for the amplification of long-chain DNA as per the attached protocol. The GenBank database was then searched for H-2K$^b$ gene needed for the construction of chimeric HLA gene, which revealed that said gene was divided in two segments registered under the Accession Nos. v00746 and v00747. As v00746, the upstream 1594 bp region of H-2K$^b$ down to midstream of intron 3 was registered and, as v00747, the downstream 1837 bp region of H-2K$^b$ down to midstream of intron 7 was registered. Because there was no BamHI restriction site in intron 3, which is divided and registered as v00746 and v00747, the H-2K$^b$ gene registered at the database was thought to have incomplete length.

There are homologous pseudogenes or highly homologous genes of H-2K$^b$ gene (Cell., 25:683, 1981). PCR was conducted with TaKaRa LA Taq™ (Takara Shuzo) as per attached protocol using the upstream primer H-2KB F3:

```
                              (30mer, SEQ ID NO:6)
5'-CGC AGG CTC TCA CAC TAT TCA GGT GAT CTC-3'
``` which has low homology with said complementary gene and is coded by exon 3 of v00746, and the downstream primer H-2KB 3R:

```
                              (38mer, SEQ ID NO:7)
5'-CGG AAT TCC GAG TCT CTG ATC TTT AGC CCT GGG GGC
TC-3'
``` which corresponds to v00747 having EcoRI restriction site added at the terminus, and, as a template, the purified mouse genomic DNA above. The PCR comprised 35 cycles of reaction at 98° C. for 10 seconds and 66° C. for 4 minutes, and reaction at 68° C. for 10 minutes, followed by cooling to 4° C.

The amplified gene fragment was ligated into KpnI and EcoRI restriction sites of phagemid vector pBluescript to obtain a recombinant plasmid. The recombinant plasmid was introduced into E. coli JM109 (Toyobo) by heat shock method at 42° C., and white colonies of E. coli to which the recombinant plasmid has been introduced were selected on ampicillin-containing LB agar medium coated with X-Gal and IPTG to obtain the transformants. Three transformants were incubated overnight in LB medium containing ampicillin (3 ml). The plasmid clone contained in each transformant was purified and subjected to analysis of nucleotide sequence in a similar manner to the above. The nucleotide sequence of respective clones and that of v00747 were compared, which revealed that there was one PCR mutation independently in two clones and three PCR mutations in one clone. There were five nucleotides commonly found in these three clones, which were different from those of v00747. These nucleotides were found in regions corresponding to intron 6 and 3' non-coding region. Furthermore, the unregistered intron 3 region contained a nucleotide resulted from PCR mutation that is different among 3 clones. The determination of nucleotide sequence was therefore partly impossible concerning the unregistered region, which could be achieved after re-cloning the unregistered intron 3 region using a polymerase with high 3'→15' exonuclease activity.

(2) Determination of Nucleotide Sequence of H-2K$^b$ Intron 3

To determine the nucleotide sequence of the unregistered region, a region containing the unregistered intron 3 region was cloned by PCR with Native Pfu DNA Polymerase (Stratagene) as per attached protocol using the purified mouse genomic DNA as a template. The PCR was carried out using an upstream primer H-2 kb F5:

5'-AGG ACT TGG ACT CTG AGA GGC AGG GTC TT-3' (29mer, SEQ ID NO:8), which is registered as v00746, and the downstream primer H-2 kb 5R:

```
                              (30mer, SEQ ID NO:9)
5'-CAT AGT CCC CTC CTT TTC CAC CTG TGA GAA-3',
``` which is registered as v00747. The PCR comprised heat treatment at 95° C. for 45 seconds, 25 cycles of reaction at 95° C. for 45 seconds, 68° C. for 1 minute and 72° C. for 4 minutes, and reaction at 72° C. for 10 minutes, followed by cooling to 4° C. The amplified gene fragment was ligated into BamHI and BglII restriction sites of phagemid vector pBluescript to obtain a recombinant plasmid. The recombinant plasmid was introduced into E. coli JM109 (Toyobo) by heat shock method at 42° C., and white colonies of E. coli to which the recombinant plasmid has been introduced were selected on ampicillin (50 µg/ml)-containing LB agar medium (1% bacto-tryptone, 0.5% yeast extract, 1% NaCl, 2% agar) coated with X-Gal and IPTG to obtain the transformants. Five transformants were incubated overnight in LB medium containing ampicillin (3 ml) and the plasmid clone contained in each transformant was purified and subjected to analysis of nucleotide sequence in a similar manner to the above. The intron 3 regions of respective clones analyzed were compared, which revealed that the sequences agreed completely. The nucleotide sequence of intron 3 region was thus determined. In addition, the region spanning from the BamHI site in the unregistered region to v00747 revealed to be 463 bp.

(3) Construction of H-2K$^b$ Genomic DNA

Figure 1:
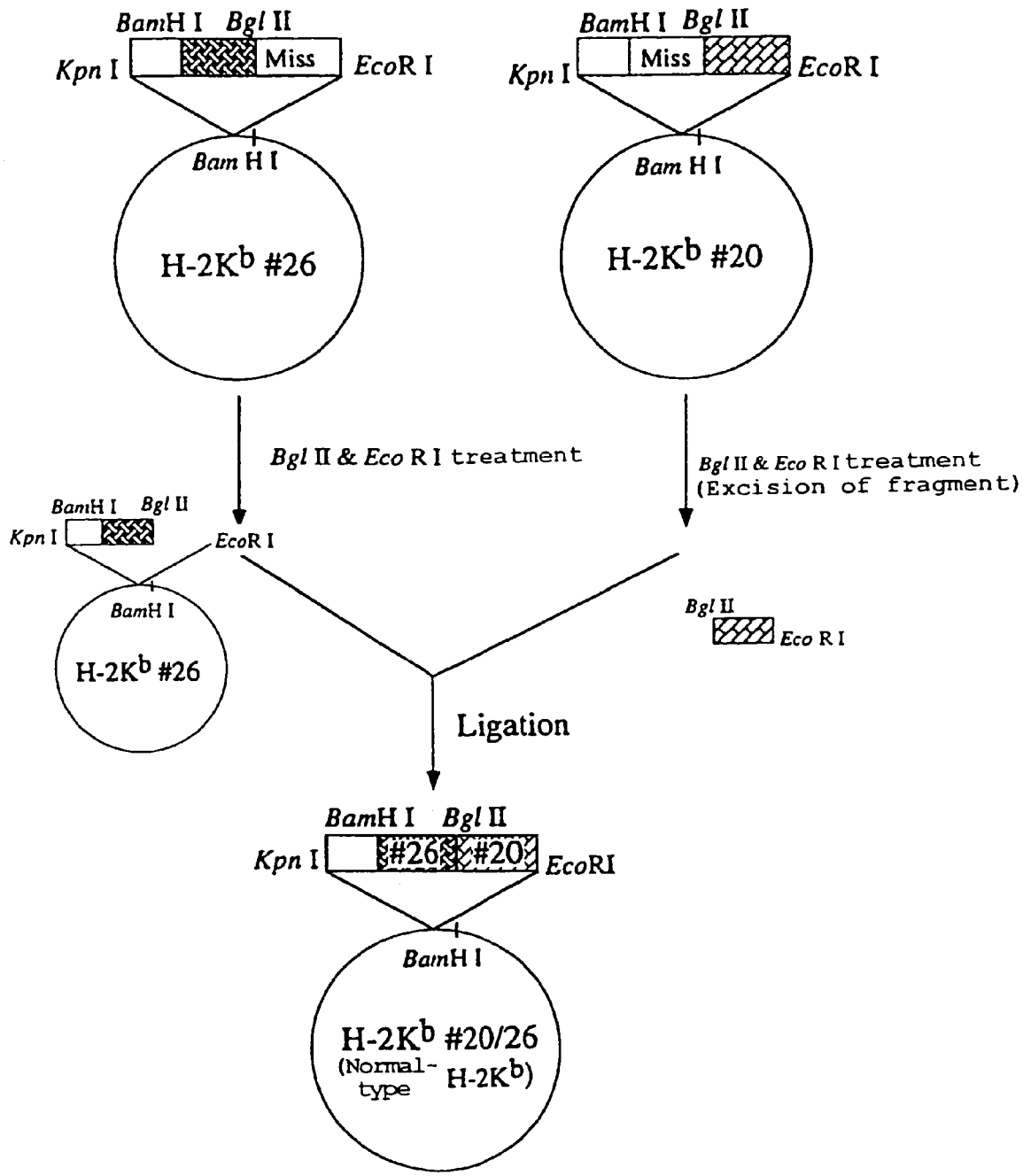
FIG. 1 is a schematic diagram showing the process for constructing an H-2K$^b$ genomic DNA used for constructing the chimera gene (HLA-A2402/K$^b$ gene) of the present invention.

As a result of determination of nucleotide sequence of the unregistered region in (2) above, the entire nucleotide sequence of H-2K$^b$ genomic DNA necessary for the construction of the objective chimeric HLA gene was determined. It became clear that the objective H-2K$^b$ genomic DNA can be constructed by combining two clones obtained in the above, i.e., H-2K$^b$#20 free of PCR mutation and H-2K$^b$#26 free of PCR mutation, in 5'- and 3'-regions, respectively. Accordingly, these clones were cleaved by a restriction enzyme and respective regions having no PCR mutations were combined to construct the H-2K$^b$ genomic DNA free of PCR mutations. The schematic diagram for construction is shown in FIG. 1.

The both clones were cleaved at the BglII and EcoRI restriction sites and ligated to obtain recombinant plasmid. The recombinant plasmid was introduced into E. coli JM109 (Toyobo) by heat shock method at 42° C., and white colonies of E. coli to which the recombinant plasmid has been introduced were selected on ampicillin-containing LB agar medium coated with X-Gal and IPTG to obtain the transformants. Three transformants were incubated overnight in LB medium containing ampicillin (3 ml). The plasmid clone contained in each transformant was purified by alkaline lysis method and subjected to sequence analysis in a similar manner to the above. As a result, it was revealed that all the transformants contained a plasmid encoding H-2K$^b$ genomic DNA free of PCT mutation.

The nucleotide sequence of H-2K$^b$ genomic DNA herein obtained corresponds to the nucleotide sequence downstream from the nucleotide at position 1551 of SEQ ID NO: 1 inclusive, which is described below.

EXAMPLE 3

Construction of Chimera Genomic DNA (HLA-A2402/K$^b$ DNA)

Figure 2:
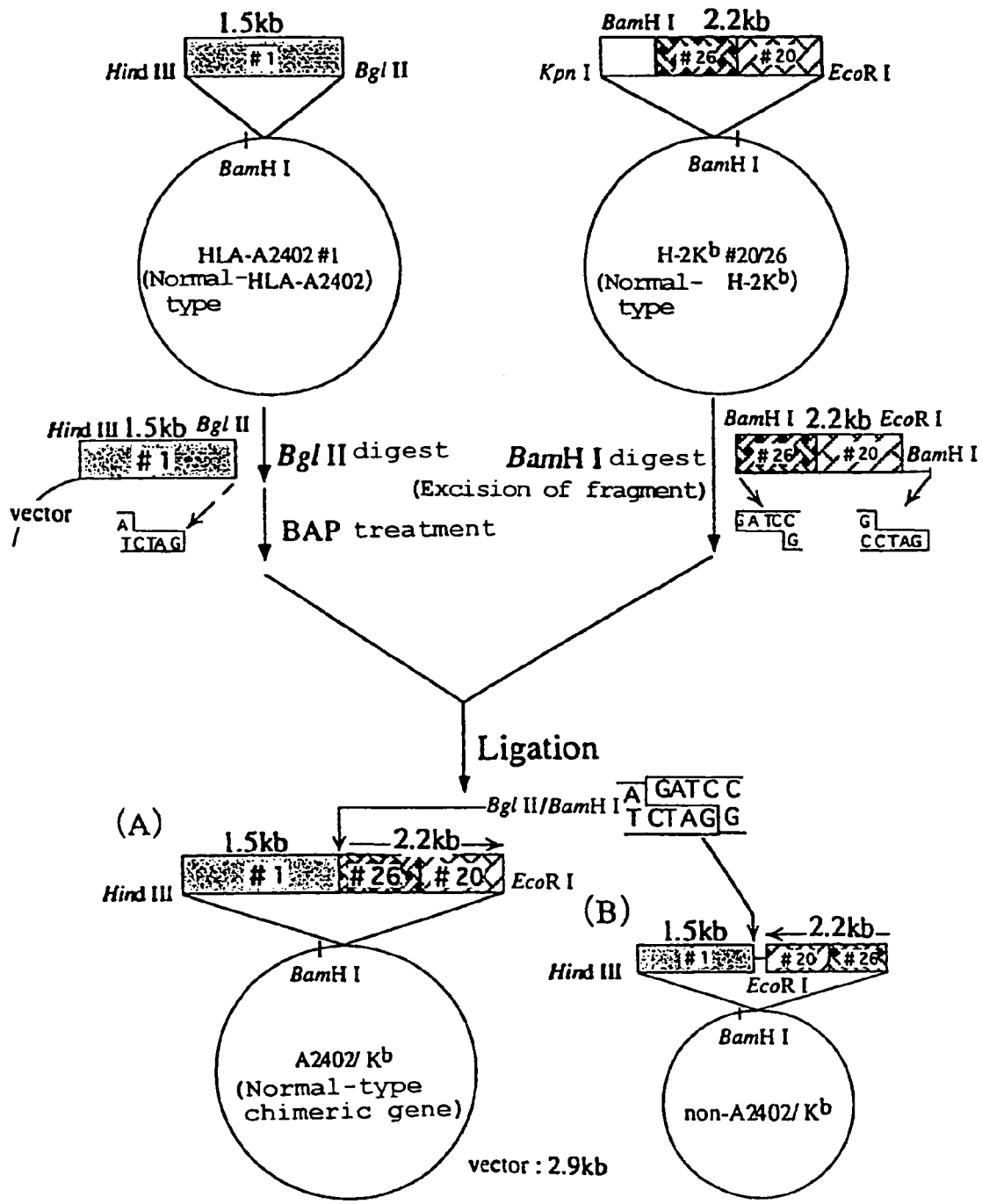
FIG. 2 is a schematic diagram showing the process for constructing the HLA-A2402/K$^b$ gene of the present invention. Plasmid H-2K$^b$#20/26 containing H-2K$^b$ genomic DNA was cleaved at BamHI site and the isolated BamHI fragment was ligated into BglII-cleaved plasmid HLA-A2402#1 containing HLA-A24 genomic DNA to construct the recombinant plasmid HLA-A2402/K$^b$. Plasmid non-A2402/K$^b$ was generated by ligating the BamHI fragment of plasmid H-2K$^b$#20/26 into plasmid HLA-A2402#1 cleaved at BglII site in the opposite orientation.

The Plasmid HLA-A2402#1 containing HLA-A2402 genomic DNA obtained in Example 1 was cleaved at BglII restriction site and the plasmid H-2K$^b$#20/26 containing H-2K$^b$ genomic DNA obtained in Example 2 was cleaved at BamHI restriction site, and the resultant fragments were ligated to give a recombinant plasmid. The schematic construction is shown in FIG. 2. The recombinant plasmid was introduced into *E. coli* JM109 (Toyobo) by heat shock method at 42° C., and white colonies of *E. coli* to which the recombinant plasmid has been introduced were selected on ampicillin-containing LB agar medium coated with X-Gal and IPTG to obtain the transformants. Ten transformants were incubated overnight in LB medium containing ampicillin (3 ml). The plasmid clone contained in each transformant was purified and subjected to sequence analysis in a similar manner to the above. As a result, it was revealed that three transformants contained a plasmid carrying the intended chimeric gene HLA-A2402/K$^b$ DNA, which may be referred to as simply "A2402/K$^b$ DNA". The genomic sequence of the constructed HLA-A2402/K$^b$ is shown in SEQ ID NO: 1.

EXAMPLE 4

Splicing Analysis of Chimera Genomic DNA

Mouse tumor cell line EL4 was transfected with the constructed chimeric HLA gene (HLA-A2402/K$^b$ gene) with Electro Gene Transfer GTE-10 (Shimadzu) as per the attached protocol. Two days later, total RNA was purified from transfected EL4 cells and un-transfected EL4 cells (control) by using ISOGEN (Nippon Gene) as per the attached protocol. Reverse transcription was performed using SuperScript Choice System (GIBCO BRL) as per the attached protocol using Oligo(dT)$_{12-18}$ and a part of said RNA as a template to synthesize cDNA. In addition, chimera gene was specifically amplified by PCR using Native Pfu DNA Polymerase (Stratagene) and a part of said cDNA as a template.

PCR was conducted using an upstream primer Chimera-F2: 5'-CGA ACC CTC GTC CTG CTA CTC TC-3' (23mer, SEQ ID NO:10), which is encoded in exon 1 of HLA-A2402 gene and has low homology with H-2K$^b$ gene, and a downstream primer Chimera-R2: 5'-AGC ATA GTC CCC TCC TTT TCC AC-3' (23mer, SEQ ID NO:11), which is encoded in exon 8 of H-2K$^b$ gene and has low homology with HLA-A2402 gene, under the conditions of heat treatment at 95° C. for 45 seconds, 40 cycles of reaction at 95° C. for 45 seconds, 53° C. for 1 minute and 72° C. for 2 minutes, and reaction at 72° C. for 10 minutes, followed by cooling to 4° C.

As a result, about 1.1 kbp gene fragments were specifically amplified only in transfected EL4 cells. Based on this result, it was estimated that the transferred chimera genomic DNA was transcribed in mouse cells, that is, HLA promoter functioned and mRNA spliced at the predicted position was expressed. The amplified fragment by PCR above was sequenced, and whereby the nucleotide sequence of cDNA encoding HLA-A2402/K$^b$ was determined as expected. The nucleotide sequence of cDNA encoding said HLA-A2402/K$^b$ is shown in SEQ ID NO:2 and the amino acid sequence thereof in SEQ ID NO:3. Furthermore, FIG. 3(A) to 3(P) show the relationship between the genome sequence of HLA-A2402/K$^b$ (SEQ ID NO: 1) and the cDNA sequence (SEQ ID NO:2) aligned in parallel. In the figure, the upper line is HLA-A2402/K$^b$ genome sequence shown in SEQ ID NO: 1 and the lower line is HLA-A2402/K$^b$ cDNA sequence shown in SEQ ID NO: 2.

EXAMPLE 5

Preparation of DNA Solution for Microinjection

Plasmid (11 µg) encoding the constructed chimeric HLA gene was digested with restriction enzymes HindIII and EcoRI, and also restriction enzyme DraI that cleaves only vector. After gel electrophoresis (1% SeaKem GTG, Nippon Gene), gel fragment containing chimera DNA was recovered. A DNA solution for microinjection was prepared by purifying the transgene with Prep-A-Gene purification kit (BioRad) as per the attached protocol and dissolving in 1/10 TE buffer (10 mM Tris (pH 8), 0.1 mM EDTA (pH 8)).

EXAMPLE 6

Introduction into Mouse Fertilized Egg and Identification of Transgenic Mouse The injection of chimera gene construct was performed using fertilized eggs derived from a C57BL/6 mouse strain.

The fertilized eggs of C57BL/6 mouse strain were used because C57BL/6 mice express as the class I molecule H-2b not H-2K$^d$ having similar binding motifs to HLA-A2402. Accordingly, a transgenic mouse of said C57BL/6 line can advantageously avoid cross reaction when an HLA-A24-binding tumor antigen peptide is administered, because the endogenous mouse class I cannot present said peptide on the cell surface.

In the first injection, the chimera construct was injected into 81 fertilized eggs, and the eggs were transferred to 4 recipient mice, which resulted in no delivery.

In the second injection, the chimera construct was injected into 50 fertilized eggs, and the eggs were transferred to 2 recipient mice, which resulted in delivery of 4 offspring, but all of them died before weaning.

In the third injection, the chimera construct was injected into 101 fertilized eggs, and the eggs were transferred to 4 recipient mice, which resulted in delivery of 11 offspring, but all of them died before weaning.

In the fourth injection, the chimera construct was injected into 168 fertilized eggs, and the eggs were transferred to 6 recipient mice, which resulted in delivery of 22 offspring, and 19 of them were weaned from the breast. Four of them, i.e., 01-4, 04-2, 05-1 and 05-6 were identified as a transgenic mouse; however, 01-4 mouse was unable to mate due to malformation and 05-6 mouse died shortly after weaning.

In the fifth injection, the chimera construct was injected into 221 fertilized eggs, and the eggs were transferred to 8 recipient mice, which resulted in delivery of 14 offspring, and 6 of them were weaned from the breast. Three of them, i.e., 04-1, 04-5 and 04-6 were identified as a transgenic mouse.

In the sixth injection, the chimera construct was injected into 225 fertilized eggs, and the eggs were transferred to 8 recipient mice, which resulted in delivery of 13 offspring, and 9 of them were weaned from the breast. Three of them, i.e., 10-5, 14-1 and 15-2 were identified as a transgenic mouse.

The transgenic mouse was identified by carrying out PCR with TaKaRa LA Taq™ (Takara Shuzo) as per the attached protocol using the same primers as those used for cloning of HLA-A2402 gene (HLA26-1F, SEQ ID NO: 4; and A24-BglII30, SEQ ID NO: 5) and a tail DNA preparation as a template, applying to 1% agarose gel electrophoresis, and selecting a mouse on the basis of the existence of 1.5 kbp DNA band.

EXAMPLE 7

Expression of Transgene Product in Transgenic Mouse

Splenocytes were recovered from spleens isolated from mice of 8 transgenic lines 04-2, 05-1, 04-1, 04-5, 04-6, 10-5, 14-1 and 15-2 constructed in Example 6, according to CURRENT PROTOCOLS IN IMMUNOLOGY, edited by J. E. Coliganl et al., John Wiley & Sons, Inc. Expression of HLA-A2402/$K^b$, which is a protein derived from transgene, on the cell surface of transgenic mouse splenocytes was analyzed by flow cytometry. As control, splenocytes prepared from C57BL/6 strain were used. Specifically, $5×10^6$ splenocytes were stained by FITC-labeled anti-HLA antibody B9.12.1 (Immunotech). Endogenous mouse class I was stained by FITC-labeled anti-H-$2K^b$ monoclonal antibody AF6-88.5 (Pharmingen).

As a result, 5 lines, i.e., 04-1, 04-5, 10-5, 14-1 and 15-2 showed expression specific for HLA class I. Among them, only 04-1 line revealed to have ability of reproduction. On the other hand, the other 3 lines, i.e., 04-6, 04-2 and 05-1, showed no expression specific for HLA class I. Thus, 8 transgenic mouse lines were constructed but, among them, only 04-1 line showed class I expression manner and achieved homozygosity.

EXAMPLE 8

Establishment of Transformed Cells Expressing HLA-A2402

A transformed cell Jurkat-A2402/$K^b$ which stably expresses HLA-2402/$K^b$ was established in order to evaluate the CTL inducing ability of the transgenic mouse prepared in the above.

(1) Construction of Expression Vector

Spleen was removed from a Tg mouse and splenocytes were prepared. Total RNA was prepared with ISOGEN (Nippon Gene) as per the attached protocol. Reverse transcription was then performed with SuperScript Choice System (GIBCO BRL) as per the attached protocol using Oligo(dT)$_{12-18}$ and, as a template, a part of said RNA to synthesize cDNA. PCR was then conducted by LA-PCR kit (Takara Shuzo) as per the attached protocol using a part of said cDNA as a template, and the upstream primer chi.PF1:

5'-CCC AAG CTT CGC CGA GGA TGG CCG TCA TGG CGC CCC GAA-3' (SEQ ID NO: 12); and the downstream primer chi.PR1:

5'-CCG GAA TTC TGT CTT CAC GCT AGA GAA TGA GGG TCA TGA AC-3', SEQ ID NO: 13). PCR comprised heat treatment at 95° C. for 45 seconds, 25 cycles of reaction at 95° C. for 45 seconds, 60° C. for 1 minute and 68° C. for 2 minutes, and reaction at 72° C. for 10 minutes, followed by cooling to 4° C. The PCR amplified gene was introduced into an expression vector pcDNA3.1(+) (Invitrogen) to construct an expression vector encoding HLA-A2402/$K^b$.

(2) Introduction into Jurkat Cells

The vector above (10 μg) was linearized by digesting with PvuI restriction enzyme. Jurkat cells (ATCC T1B-152) $5×10^6$ were transfected with the constructed chimeric HLA gene by means of a gene-transfer device (GIBCO BRL) as per the attached protocol. Cells were seeded into 96-well plate at 0.5 cells/well and cultured in a medium containing Geneticin (0.6 mg/ml). As a result, cell proliferation was observed in 6 wells (6 clones, A-2, A-4, A-6, A-9, A-10 and A-11). Among them, A-10 showed the highest expression of transgene and said clone was established as Jurkat-A2402/Kb cell.

EXAMPLE 9

Test for CTL Inducing Ability of Transgenic Mouse

Human tumor antigen HER-2/neu is known to be overexpressed in breast, ovarian and lung cancers, and is shown by in vitro experiment that a peptide derived therefrom has an activity of inducing specific CTLs in peripheral blood of HLA-A24 positive healthy subjects (Int. J. Cancer., 87:553, 2000).

The transgenic mouse was immunized with HLA-A24-binding peptide HER-2/neu$_{780-788}$ (SEQ ID NO: 14) derived from said human tumor antigen and MHC Class II I-$A^b$-restricted helper peptide originated from tetanus toxin (FN-NFTVSFWLRVPKVSASHLE) (SEQ ID NO: 21), and examined whether specific CTLs are induced as is the case with human. That is, HER-2/neu$_{780-788}$ and helper peptide were adjusted to 40 mg/ml and 20 mg/ml, respectively, in DMSO and diluted with physiological saline to 2 mg/ml and 1 mg/ml, respectively. They were mixed with equal amount of Freund's incomplete adjuvant (Wako Pure Chemical Industries, Ltd.) using glass syringe to prepare water-in-oil emulsion. The resultant preparation (200 μl) was injected into a transgenic mouse (04-1 line) subcutaneously in the base of the tail for immunization. Seven days after initiation of experiment, spleen was removed and grounded on the frosted part of glass slide, and splenocytes were recovered and prepared. A portion of splenocytes undergone hemolysis treatment with ACK buffer (0.15 M NH$_4$Cl, 10 mM KHCO$_3$, 0.1 mM EDTA, pH 7.2-7.4) was exposed to X ray radiation (2,000 rad), pulsed with the above-mentioned peptide (100 μg/ml) for 1 hour, and seeded into 24-well plate at $0.7×10^6$/well. Non-radiated, non-peptide-pulsed splenocytes ($7×10^6$/well) were added together and stimulated again at 37° C. (final concentration of peptide, 1 μg/ml). In vitro stimulation was carried out for 6 days in 10 ml of a culture solution (CTM culture solution) containing 10% FCS, 10 mM HEPES, 20 mM L-glutamine, 1 mM sodium pyruvate, 1 mM MEM nonessential amino acid, 1% MEM vitamin and 55 μM 2-mercaptoethanol in RPMI1640 medium.

On the other hand, Jurkat-A2402/$K^b$ cells prepared in Example 8 were labeled with $^{51}$Cr (3.7 MBq/$10^6$ cells) and pulsed with the peptide above at 100 μg/ml for one hour. The labeling was carried out over 2 hours, and 1 hour after initiation of labeling, peptide was added to make the final concentration 100 μg/ml. Cells that were not pulsed with peptide were prepared as control target cells.

CTL-inducing activity was determined by $^{51}$Cr release assay (J. Immunol., 159:4753, 1997), wherein the previously prepared transgenic mouse splenocyte preparation was added to said Jurkat-A2402/$K^b$ cells as the target cells. The results are shown in FIG. 4. As a result, induction of specific CTLs by stimulation with HER-2/neu$_{780-788}$ was observed.

Furthermore, the CTL inducing ability was tested in the same manner using MAGE-3$_{195-203}$ (SEQ ID NO: 18), CEA$_{652-660}$ (SEQ ID NO: 19) and CEA$_{268-277}$ (SEQ ID NO: 20), which are also known to be HLA-A24-binding tumor antigen peptide like HER-2/neu$_{780-788}$. The results are shown in FIG. 5 to FIG. 7. As a result, induction of specific CTLs by stimulation with these known HLA-A24-binding tumor antigen peptides was observed.

From these results, the HLA-A24 transgenic mouse of the present invention were revealed to be an animal model for human that can be used for evaluation of HLA-A24-binding tumor antigen protein or tumor antigen peptide.

EXAMPLE 10

CTL Induction by Tumor Antigen PSA-Originated Peptide

Since it was found that the HLA-A24 transgenic mouse of the present invention makes it possible to evaluate HLA-A24-binding tumor antigen protein or tumor antigen peptide in vivo, evaluation of peptides that have not been identified as a tumor antigen peptide yet was conducted using said mouse. In the Experiment, peptides originated from human tumor antigen PSA were used. There have not been any reports regarding HLA-A24-binding tumor antigen peptide PSA originated from regions so far.

The amino acid sequence of PSA protein was searched for the sequence corresponding to human HLA-A24-binding motifs, that is, a motif wherein the 2nd amino acid is tyrosine, phenylalanine, methionine or tryptophan and the C-terminal amino acid is phenylalanine, tryptophan, leucine, isoleucine or methionine, and two kinds of sequences consisting of 9 amino acids or 10 amino acids (PSA$_{152-160}$: SEQ ID NO:15 and PSA$_{248-257}$: SEQ ID NO:16) were identified. Said PSA$_{152-160}$ and PSA$_{248-257}$ correspond to partial sequences of amino acid Nos. 152-160 and 248-257, respectively, of the amino acid sequence of PSA.

Tumor antigenicity of PSA$_{152-160}$ or PSA$_{248-257}$ was analyzed using HLA-A2402/K$^b$ transgenic mouse of 04-1 line constructed in Example 7. A transgenic mouse was immunized with PSA$_{152-160}$ or PSA$_{248-257}$ in association with tetanus toxin-derived mouse MHC class II I-A$^b$-restricted helper peptide (FNNFTVSFWLRVPKVSASHLE) (SEQ ID NO: 21), and the CTL-inducing activity was determined in a manner similar to that described in Example 9. FIGS. 8 and 9 show the results of determination of CTL induction by PSA$_{152-160}$, and PSA$_{248-257}$, respectively. PSA$_{152-360}$ caused specific CTL induction but PSA$_{248-257}$ did not. Accordingly, it became evident that PSA$_{152-160}$ has tumor antigenicity in vivo, in other words, it is an HLA-A24-binding tumor antigen peptide. The results above also demonstrate that peptides having the binding motif of HLA-A24 type do not necessarily have antigenicity in vivo and that the present method is useful for identifying active peptides.

Sequence Listing Free Text

In the nucleotide sequence shown in SEQ ID NO: 1, the region between No. 1 and No. 1550 is of human origin, and the region between No. 1551 and No. 3587 is of mouse origin.

In the nucleotide sequence shown in SEQ ID NO: 2, the region between No. 1 and No. 618 is of human origin and the region between No. 619 and No. 1119 is of mouse origin.

In the amino acid sequence shown in SEQ ID NO: 3, the region between No. 1 and No. 206 is of human origin and the region between No. 207 and No. 372 is of mouse origin.

The nucleotide sequence shown in SEQ ID NO: 4 is a PCR primer.

The nucleotide sequence shown in SEQ ID NO: 5 is a PCR primer.

The nucleotide sequence shown in SEQ ID NO: 6 is a PCR primer.

The nucleotide sequence shown in SEQ ID NO: 7 is a PCR primer.

The nucleotide sequence shown in SEQ ID NO: 8 is a PCR primer.

The nucleotide sequence shown in SEQ ID NO: 9 is a PCR primer.

The nucleotide sequence shown in SEQ ID NO: 10 is a PCR primer.

The nucleotide sequence shown in SEQ ID NO: 11 is a PCR primer.

The nucleotide sequence shown in SEQ ID NO: 12 is a PCR primer.

The nucleotide sequence shown in SEQ ID NO: 13 is a PCR primer.

In the amino acid sequence of SEQ ID NO: 17, the second amino acid is phenylalanine, tyrosine, methionine or tryptophan, and the ninth amino acid is phenylalanine, leucine, isoleucine, tryptophan or methionine.

INDUSTRIAL APPLICABILITY

According to the present invention, it is provided transgenic mice which have had an HLA-A24 gene introduced and in which CTL is induced in response to stimulation with an HLA-A24-binding antigen, a method of screening a therapeutic or preventive agent for tumors or virus infections using said transgenic mice, and HLA-A24-binding tumor antigen peptides of PSA origin selected by the screening method.

The invention claimed is:

1. A transgenic mouse comprising a chimera gene comprising α1 and α2 domains of an HLA-A2402 gene and the α3 domain of a mouse H-2K$^b$ gene wherein cytotoxic T lymphocytes of the mouse induce an HLA-A2402-specific cytotoxic response when stimulated with HLA-A2402, wherein said chimera gene comprises a nucleotide sequence selected from the group consisting of (a) a nucleotide sequence that encodes the amino acid sequence set forth in SEQ ID NO: 3, (b) the nucleotide sequence set forth in SEQ ID NO: 2, and (c) the nucleotide sequence set forth in SEQ ID NO: 1.

2. The transgenic mouse according to claim 1, wherein the mouse is of C57BL/6 mouse strain.

* * * * *

SEQUENCE LISTING

<160> NUMBER OF SEQ ID NOS: 21

<210> SEQ ID NO 1
<211> LENGTH: 3857
<212> TYPE: DNA
<213> ORGANISM: Artificial Sequence
<220> FEATURE:
<223> OTHER INFORMATION: Description of Artificial Sequence: The DNA
      region from position 1 to position 1550 is derived from human, and
      the DNA region from position 1551 to position 3857 is derived from
      mouse.

<400> SEQUENCE: 1

```
aagcttactc tctggcacca aactccatgg gatgattttt cttctagaag agtccaggtg      60
gacaggtaag gagtgggagt cagggagtcc agttcaggga cagagattac gggatgaaaa     120
gtgaaaggag agggacgggg cccatgccga gggtttctcc cttgtttctc agacagctct     180
tgggccaaga ttcagggaga cattgagaca gagcgcttgg cacagaagca gaggggtcag     240
ggcgaagtcc cagggcccca ggcgtggctc tcagggtctc aggccccgaa ggcggtgtat     300
ggattgggga gtcccagcct tggggattcc ccaactccgc agtttctttt ctccctctcc     360
caacctatgt agggtccttc ttcctggata ctcacgacgc ggacccagtt ctcactccca     420
ttgggtgtcg ggtttccaga gaagccaatc agtgtcgtcg cggtcgctgt tctaaagtcc     480
gcacgcaccc accgggactc agattctccc cagacgccga ggatggccgt catggcgccc     540
cgaaccctcg tcctgctact ctcggggggcc ctggccctga cccagacctg gcaggtgag     600
tgcggggtcg ggagggaaac ggcctctgcg gggagaagca aggggcccgc ctggcggggg     660
cgcaagaccc gggaagccgc gccgggagga gggtcgggcg ggtctcagcc actcctcgtc     720
cccaggctcc cactccatga ggtatttctc cacatccgtg tcccggcccg gccgcgggga     780
gccccgcttc atcgccgtgg gctacgtgga cgacacgcag ttcgtgcggt tcgacagcga     840
cgccgcgagc cagaggatgg agccgcgggc gccgtggata gagcaggagg ggccggagta     900
ttgggacgag gagacaggga aagtgaaggc ccactcacag actgaccgag agaacctgcg     960
gatcgcgctc cgctactaca accagagcga ggccggtgag tgaccccggc ccggggcgca    1020
ggtcacgacc cctcatcccc cacggacggg ccgggtcgcc cacagtctcc gggtccgaga    1080
tccaccccga agccgcggga ccccgagacc cttgccccgg gagaggccca ggcgccttaa    1140
cccggtttca ttttcagttt aggccaaaaa tccccccggg ttggtcgggg ccgggcgggg    1200
ctcgggggac tgggctgacc gcggggtcgg ggccaggttc tcacaccctc cagatgatgt    1260
ttggctgcga cgtggggtcg gacgggcgct tcctccgcgg gtaccaccag tacgcctacg    1320
acggcaagga ttcatcgcc ctgaaagagg acctgcgctc ttggaccgcg gcggacatgg    1380
cggctcagat caccaagcgc aagtgggagg cggcccatgt ggcggagcag cagagagcct    1440
acctggaggg cacgtgcgtg gacgggctcc gcagatacct ggagaacggg aaggagacgc    1500
tgcagcgcac gggtaccagg ggccacgggg cgcctacctg atcgcctgta gatcctgtgt    1560
gacacacctg taccttgtcc cccagagtca ggggctggga gtcatttct ctggctacac    1620
acttagtgat ggctgttcac ttggactgac agttaatgtt ggtcagcaag gtgactacaa    1680
tggttgagtc tcaatggtgt caccttccag gatcatacag ccctaatttt aatatgaact    1740
caaacacata ttaaattagt tattttccat tccctcctcc attctttgac tacctctctc    1800
atgctattga acatcacata aggatggcca tgtttaccca atggctcatg tggattccct    1860
cttagcttct gagtcccaaa agaaaatgtg cagtcctgtg ctgaggggac cagctctgct    1920
tttggtcact agtgcgatga cagttgaagt gtcaaacaga cacatagttc actgtcatca    1980
ttgatttaac tgagtcttgg gtagatttca gtttgtcttg ttaattgtgt gatttcttaa    2040
atcttccaca cagattcccc aaaggcccat gtgacccatc acagcagacc tgaagataaa    2100
gtcaccctga ggtgctgggc cctgggcttc taccctgctg acatcaccct gacctggcag    2160
ttgaatgggg aggagctgat ccaggacatg gagcttgtgg agaccaggcc tgcaggggat    2220
ggaaccttcc agaagtgggc atctgtggtg gtgcctcttg gaaggagca gtattacaca    2280
```

```
tgccatgtgt accatcaggg gctgcctgag cccctcaccc tgagatgggg taaggagagt    2340
gtgggtgcag agctggggtc agggaaagct ggagctttct gcagaccctg agctgctcag    2400
ggctgagagc tggggtcatg accctcacct tcatttcttg tacctgtcct tcccagagcc    2460
tcctccatcc actgtctcca acatggcgac cgttgctgtt ctggttgtcc ttggagctgc    2520
aatagtcact ggagctgtgg tggcttttgt gatgaagatg agaaggagaa acacaggtag    2580
gaaagggcag agtctgagtt ttctctcagc ctcctttaga gtgtgctctg ctcatcaatg    2640
gggaacacag gcacacccca cattgctact gtctctaact gggtctgctg tcagttctgg    2700
gaacttccta gtgtcaagat cttcctggaa ctctcacagc ttttcttctc acaggtggaa    2760
aaggagggga ctatgctctg gctccaggtt agtgtgggga cagagttgtc ctggggacat    2820
tggagtgaag ttgagatga tgggagctct gggaatccat aatagctcct ccagagaaat    2880
cttctaggtg cctgagttgt gccatgaaat gaatatgtac atgtacatat gcatatacat    2940 ttgtttttgtt ttaccctagg ctcccagacc tctgatctgt ctctcccaga ttgtaaaggt    3000
gacactctag ggtctgattg gggagggcca atgtggacat gattgggttt caggaactcc    3060
cagaatcccc tgtgagtgag tgatgggttg ttcgaatgtt gtcttcacag tgatggttca    3120
tgaccctcat tctctagcgt gaagacagct gcctggagtg gacttggtga cagacaatgt    3180
cttctcatat ctcctgtgac atccagagcc ctcagttctc tttagtcaag tgtctgatgt    3240
tccctgtgag cctatggact caatgtgaag aactgtggag cccagtccac ccctctacac    3300
caggaccctg tccctgcact gctctgtctt cccttccaca gccaaccttg ctggttcagc    3360
caaacactga gggacatctg tagcctgtca gctccatgct accctgacct gcaactcctc    3420
acttccacac tgagaataat aatttgaatg taaccttgat tgttatcatc ttgacctagg    3480
gctgatttct tgttaatttc atggattgag aatgcttaga ggttttgttt gtttgtttga    3540
ttgatttgtt tttttgaaga ataaatgat agatgaataa acttccagaa tctgggtcac    3600
tatgctgtgt gtatctgttg ggacaggatg agactgtagc agctgagtgt gaacagggct    3660
gtgccgaggt gggctcagtt tgctttgatc tgtgatgggg ccacacctcc actgtgtcac    3720
ctctgggctc tgttccctct atcactatga ggcacatgct gagagtttgt ggtcacaaag    3780
acacagggaa ggcctgagcc ttgccctgtc cccaggatta tgagcccca gggctaaaga    3840 tcagagactc ggaattc                                                   3857
```

<210> SEQ ID NO 2
<211> LENGTH: 1119
<212> TYPE: DNA
<213> ORGANISM: Artificial Sequence
<220> FEATURE:
<223> OTHER INFORMATION: Description of Artificial Sequence: The DNA
      region from position 1 to position 618 is derived from human, and
      the DNA region from position 619 to position 1119 is derived from
      mouse.

<400> SEQUENCE: 2

```
atg gcc gtc atg gcg ccc cga acc ctc gtc ctg cta ctc tcg ggg gcc      48
Met Ala Val Met Ala Pro Arg Thr Leu Val Leu Leu Leu Ser Gly Ala
  1               5                  10                  15 ctg gcc ctg acc cag acc tgg gca ggc tcc cac tcc atg agg tat ttc      96
Leu Ala Leu Thr Gln Thr Trp Ala Gly Ser His Ser Met Arg Tyr Phe
             20                  25                  30 tcc aca tcc gtg tcc cgg ccc ggc cgc ggg gag ccc cgc ttc atc gcc     144
Ser Thr Ser Val Ser Arg Pro Gly Arg Gly Glu Pro Arg Phe Ile Ala
         35                  40                  45
```

```
gtg ggc tac gtg gac gac acg cag ttc gtg cgg ttc gac agc gac gcc      192
Val Gly Tyr Val Asp Asp Thr Gln Phe Val Arg Phe Asp Ser Asp Ala
         50                  55                  60 gcg agc cag agg atg gag ccg cgg gcg ccg tgg ata gag cag gag ggg      240
Ala Ser Gln Arg Met Glu Pro Arg Ala Pro Trp Ile Glu Gln Glu Gly
 65                  70                  75                  80 ccg gag tat tgg gac gag gag aca ggg aaa gtg aag gcc cac tca cag      288
Pro Glu Tyr Trp Asp Glu Glu Thr Gly Lys Val Lys Ala His Ser Gln
                 85                  90                  95 act gac cga gag aac ctg cgg atc gcg ctc cgc tac tac aac cag agc      336
Thr Asp Arg Glu Asn Leu Arg Ile Ala Leu Arg Tyr Tyr Asn Gln Ser
            100                 105                 110 gag gcc ggt tct cac acc ctc cag atg atg ttt ggc tgc gac gtg ggg      384
Glu Ala Gly Ser His Thr Leu Gln Met Met Phe Gly Cys Asp Val Gly
        115                 120                 125 tcg gac ggg cgc ttc ctc cgc ggg tac cac cag tac gcc tac gac ggc      432
Ser Asp Gly Arg Phe Leu Arg Gly Tyr His Gln Tyr Ala Tyr Asp Gly
    130                 135                 140 aag gat tac atc gcc ctg aaa gag gac ctg cgc tct tgg acc gcg gcg      480
Lys Asp Tyr Ile Ala Leu Lys Glu Asp Leu Arg Ser Trp Thr Ala Ala
145                 150                 155                 160 gac atg gcg gct cag atc acc aag cgc aag tgg gag gcg gcc cat gtg      528
Asp Met Ala Ala Gln Ile Thr Lys Arg Lys Trp Glu Ala Ala His Val
                165                 170                 175 gcg gag cag cag aga gcc tac ctg gag ggc acg tgc gtg gac ggg ctc      576
Ala Glu Gln Gln Arg Ala Tyr Leu Glu Gly Thr Cys Val Asp Gly Leu
            180                 185                 190 cgc aga tac ctg gag aac ggg aag gag acg ctg cag cgc acg gat tcc      624
Arg Arg Tyr Leu Glu Asn Gly Lys Glu Thr Leu Gln Arg Thr Asp Ser
        195                 200                 205 cca aag gcc cat gtg acc cat cac agc aga cct gaa gat aaa gtc acc      672
Pro Lys Ala His Val Thr His His Ser Arg Pro Glu Asp Lys Val Thr
    210                 215                 220 ctg agg tgc tgg gcc ctg ggc ttc tac cct gct gac atc acc ctg acc      720
Leu Arg Cys Trp Ala Leu Gly Phe Tyr Pro Ala Asp Ile Thr Leu Thr
225                 230                 235                 240 tgg cag ttg aat ggg gag gag ctg atc cag gac atg gag ctt gtg gag      768
Trp Gln Leu Asn Gly Glu Glu Leu Ile Gln Asp Met Glu Leu Val Glu
                245                 250                 255 acc agg cct gca ggg gat gga acc ttc cag aag tgg gca tct gtg gtg      816
Thr Arg Pro Ala Gly Asp Gly Thr Phe Gln Lys Trp Ala Ser Val Val
            260                 265                 270 gtg cct ctt ggg aag gag cag tat tac aca tgc cat gtg tac cat cag      864
Val Pro Leu Gly Lys Glu Gln Tyr Tyr Thr Cys His Val Tyr His Gln
        275                 280                 285 ggg ctg cct gag ccc ctc acc ctg aga tgg gag cct cct cca tcc act      912
Gly Leu Pro Glu Pro Leu Thr Leu Arg Trp Glu Pro Pro Pro Ser Thr
    290                 295                 300 gtc tcc aac atg gcg acc gtt gct gtt ctg gtt gtc ctt gga gct gca      960
Val Ser Asn Met Ala Thr Val Ala Val Leu Val Val Leu Gly Ala Ala
305                 310                 315                 320 ata gtc act gga gct gtg gtg gct ttt gtg atg aag atg aga agg aga     1008
Ile Val Thr Gly Ala Val Val Ala Phe Val Met Lys Met Arg Arg Arg
                325                 330                 335 aac aca ggt gga aaa gga ggg gac tat gct ctg gct cca ggc tcc cag     1056
Asn Thr Gly Gly Lys Gly Gly Asp Tyr Ala Leu Ala Pro Gly Ser Gln
            340                 345                 350 acc tct gat ctg tct ctc cca gat tgt aaa gtg atg gtt cat gac cct     1104
Thr Ser Asp Leu Ser Leu Pro Asp Cys Lys Val Met Val His Asp Pro
        355                 360                 365
```

```
cat tct cta gcg tga                                             1119
His Ser Leu Ala
    370
```

<210> SEQ ID NO 3
<211> LENGTH: 372
<212> TYPE: PRT
<213> ORGANISM: Artificial Sequence
<220> FEATURE:
<223> OTHER INFORMATION: Description of Artificial Sequence: The
      polypeptide region from position 1 to position 206 is derived from
      human, 207 to position 372 is derived from mouse.

<400> SEQUENCE: 3

| Met | Ala | Val | Met | Ala | Pro | Arg | Thr | Leu | Val | Leu | Leu | Leu | Ser | Gly | Ala |
|---|---|---|---|---|---|---|---|---|---|---|---|---|---|---|---|
| 1 | | | | 5 | | | | | 10 | | | | | 15 | |

| Leu | Ala | Leu | Thr | Gln | Thr | Trp | Ala | Gly | Ser | His | Ser | Met | Arg | Tyr | Phe |
| | | | 20 | | | | | 25 | | | | | 30 | | |

| Ser | Thr | Ser | Val | Ser | Arg | Pro | Gly | Arg | Gly | Glu | Pro | Arg | Phe | Ile | Ala |
| | | | 35 | | | | | 40 | | | | | 45 | | |

| Val | Gly | Tyr | Val | Asp | Asp | Thr | Gln | Phe | Val | Arg | Phe | Asp | Ser | Asp | Ala |
| | 50 | | | | | 55 | | | | | 60 | | | | |

| Ala | Ser | Gln | Arg | Met | Glu | Pro | Arg | Ala | Pro | Trp | Ile | Glu | Gln | Glu | Gly |
| 65 | | | | | 70 | | | | | 75 | | | | | 80 |

| Pro | Glu | Tyr | Trp | Asp | Glu | Thr | Gly | Lys | Val | Lys | Ala | His | Ser | Gln |
| | | | | 85 | | | | | 90 | | | | | 95 |

| Thr | Asp | Arg | Glu | Asn | Leu | Arg | Ile | Ala | Leu | Arg | Tyr | Tyr | Asn | Gln | Ser |
| | | | 100 | | | | | 105 | | | | | 110 | | |

| Glu | Ala | Gly | Ser | His | Thr | Leu | Gln | Met | Met | Phe | Gly | Cys | Asp | Val | Gly |
| | | | 115 | | | | | 120 | | | | | 125 | | |

| Ser | Asp | Gly | Arg | Phe | Leu | Arg | Gly | Tyr | His | Gln | Tyr | Ala | Tyr | Asp | Gly |
| | 130 | | | | | 135 | | | | | 140 | | | | |

| Lys | Asp | Tyr | Ile | Ala | Leu | Lys | Glu | Asp | Leu | Arg | Ser | Trp | Thr | Ala | Ala |
| 145 | | | | | 150 | | | | | 155 | | | | | 160 |

| Asp | Met | Ala | Ala | Gln | Ile | Thr | Lys | Arg | Lys | Trp | Glu | Ala | Ala | His | Val |
| | | | | 165 | | | | | 170 | | | | | 175 | |

| Ala | Glu | Gln | Gln | Arg | Ala | Tyr | Leu | Glu | Gly | Thr | Cys | Val | Asp | Gly | Leu |
| | | | 180 | | | | | 185 | | | | | 190 | | |

| Arg | Arg | Tyr | Leu | Glu | Asn | Gly | Lys | Glu | Thr | Leu | Gln | Arg | Thr | Asp | Ser |
| | | | 195 | | | | | 200 | | | | | 205 | | |

| Pro | Lys | Ala | His | Val | Thr | His | His | Ser | Arg | Pro | Glu | Asp | Lys | Val | Thr |
| | 210 | | | | | 215 | | | | | 220 | | | | |

| Leu | Arg | Cys | Trp | Ala | Leu | Gly | Phe | Tyr | Pro | Ala | Asp | Ile | Thr | Leu | Thr |
| 225 | | | | | 230 | | | | | 235 | | | | | 240 |

| Trp | Gln | Leu | Asn | Gly | Glu | Glu | Leu | Ile | Gln | Asp | Met | Glu | Leu | Val | Glu |
| | | | | 245 | | | | | 250 | | | | | 255 | |

| Thr | Arg | Pro | Ala | Gly | Asp | Gly | Thr | Phe | Gln | Lys | Trp | Ala | Ser | Val | Val |
| | | | 260 | | | | | 265 | | | | | 270 | | |

| Val | Pro | Leu | Gly | Lys | Glu | Gln | Tyr | Tyr | Thr | Cys | His | Val | Tyr | His | Gln |
| | | | 275 | | | | | 280 | | | | | 285 | | |

| Gly | Leu | Pro | Glu | Pro | Leu | Thr | Leu | Arg | Trp | Glu | Pro | Pro | Ser | Thr |
| | 290 | | | | | 295 | | | | | 300 | | | | |

| Val | Ser | Asn | Met | Ala | Thr | Val | Ala | Val | Leu | Val | Val | Leu | Gly | Ala | Ala |
| 305 | | | | | 310 | | | | | 315 | | | | | 320 |

| Ile | Val | Thr | Gly | Ala | Val | Val | Ala | Phe | Val | Met | Lys | Met | Arg | Arg | Arg |
| | | | | 325 | | | | | 330 | | | | | 335 | |

-continued

Asn Thr Gly Gly Lys Gly Gly Asp Tyr Ala Leu Ala Pro Gly Ser Gln
            340                 345                 350

Thr Ser Asp Leu Ser Leu Pro Asp Cys Lys Val Met Val His Asp Pro
        355                 360                 365

His Ser Leu Ala
    370

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 4
cccaagctta ctctctggca ccaaactcca tgggat                          36

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 5
cgggagatct acaggcgatc aggtaggcgc                                 30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 6
cgcaggctct cacactattc aggtgatctc                                 30

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 7
cggaattccg agtctctgat ctttagccct gggggctc                        38

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 8
aggacttgga ctctgagagg cagggtctt                                  29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 9

-continued

```
catagtcccc tccttttcca cctgtgagaa                                        30

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 10
cgaaccctcg tcctgctact ctc                                               23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 11
agcatagtcc cctcctttc cac                                                23

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 12
cccaagcttc gccgaggatg gccgtcatgg cgccccgaa                              39

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 13
ccggaattct gtcttcacgc tagagaatga gggtcatgaa c                           41

<210> SEQ ID NO 14
<211> LENGTH: 9
<212> TYPE: PRT
<213> ORGANISM: Homo sapiens

<400> SEQUENCE: 14

Pro Tyr Val Ser Arg Leu Leu Gly Ile
                5

<210> SEQ ID NO 15
<211> LENGTH: 9
<212> TYPE: PRT
<213> ORGANISM: Homo sapiens

<400> SEQUENCE: 15

Cys Tyr Ala Ser Gly Trp Gly Ser Ile
                5

<210> SEQ ID NO 16
<211> LENGTH: 10
<212> TYPE: PRT
<213> ORGANISM: Homo sapiens
```

```
<400> SEQUENCE: 16

His Tyr Arg Lys Trp Ile Lys Asp Thr Ile
                 5                   10

<210> SEQ ID NO 17
<211> LENGTH: 9
<212> TYPE: PRT
<213> ORGANISM: Artificial Sequence
<220> FEATURE:
<221> NAME/KEY: VARIANT
<222> LOCATION: 2
<223> OTHER INFORMATION: Xaa is Phe, Tyr, Met or Trp.
<220> FEATURE:
<221> NAME/KEY: VARIANT
<222> LOCATION: 9
<223> OTHER INFORMATION: Xaa is Phe, Leu, Ile, Trp or Met.

<400> SEQUENCE: 17

Cys Xaa Ala Ser Gly Trp Gly Ser Xaa
                 5

<210> SEQ ID NO 18
<211> LENGTH: 9
<212> TYPE: PRT
<213> ORGANISM: Homo sapiens

<400> SEQUENCE: 18

Ile Met Pro Lys Ala Gly Leu Leu Ile
                 5

<210> SEQ ID NO 19
<211> LENGTH: 9
<212> TYPE: PRT
<213> ORGANISM: Homo sapiens

<400> SEQUENCE: 19

Thr Tyr Ala Cys Phe Val Ser Asn Leu
                 5

<210> SEQ ID NO 20
<211> LENGTH: 10
<212> TYPE: PRT
<213> ORGANISM: Homo sapiens

<400> SEQUENCE: 20

Gln Tyr Ser Trp Phe Val Asn Gly Thr Phe
                 5                   10

<210> SEQ ID NO 21
<211> LENGTH: 21
<212> TYPE: PRT
<213> ORGANISM: Unknown
<220> FEATURE:
<223> OTHER INFORMATION: MHC Class II I-Ab-restricted helper peptide
      originating from tetanus toxin

<400> SEQUENCE: 21

Phe Asn Asn Phe Thr Val Ser Phe Trp Leu Arg Val Pro Lys Val Ser
 1               5                  10                  15

Ala Ser His Leu Glu
                20
```